(12) United States Patent
Jugulam et al.

(10) Patent No.: US 11,492,629 B2
(45) Date of Patent: Nov. 8, 2022

(54) EXTRA-CHROMOSOMAL CIRCULAR DNA-MEDIATED ENGINEERING OF PLANT TRAITS

(71) Applicant: Kansas State University Research Foundation, Manhattan, KS (US)

(72) Inventors: Mithila Jugulam, Manhattan, KS (US); Dal-Hoe Koo, Manhattan, KS (US); Bikram S. Gill, Manhattan, KS (US); Bernd Friebe, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 16/811,265

(22) Filed: Mar. 6, 2020

(65) Prior Publication Data
US 2020/0283787 A1    Sep. 10, 2020

Related U.S. Application Data

(60) Provisional application No. 62/814,693, filed on Mar. 6, 2019.

(51) Int. Cl.
*C12N 15/82*    (2006.01)

(52) U.S. Cl.
CPC ..... *C12N 15/8201* (2013.01); *C12N 15/8261* (2013.01)

(58) Field of Classification Search
CPC ..................................... C12N 15/82
See application file for complete search history.

(56) References Cited

PUBLICATIONS

Sundaresan et al PNAS 84:4924-4928 (Year: 1987).*
Bregeon et al BioTechniques 37:760-766 (Year: 2004).*
Koo, et al., "Extrachromosomal circular DNA-based amplification and transmission of herbicide resistance in crop weed Amaranthus palmeri", PNAS, published online Mar. 12, 2018 (6 pages).

* cited by examiner

*Primary Examiner* — Brent T Page
(74) *Attorney, Agent, or Firm* — Hovey Williams LLP

(57) ABSTRACT

Methods of modifying plants by amplifying native or introducing extrachromosomal circular plant DNA comprising one or more exogenous or endogenous genes conferring an agronomically useful trait when expressed in a plant, or disrupting the association or tethering of endogenous extrachromosomal circular plant DNA with endogenous chromosomes in a plant to change one or more plant traits.

15 Claims, 24 Drawing Sheets
(21 of 24 Drawing Sheet(s) Filed in Color)
Specification includes a Sequence Listing.

(A)

(B)

(C)

—— 12% —— —— 88% ——

—— 71.4% —————— –28.6% ——

SEQUENCE LISTING

```
<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: Synthetic forward primer

<400> SEQUENCE: 1
```

```
atgttggacg ctctcagaac tcttggt                                           27

<210> SEQ ID NO 2
<211> LENGTH: 23
<212> TYPE: DNA
<213> ORGANISM: Artificial Sequence
<220> FEATURE:
<223> OTHER INFORMATION: Synthetic reverse primer

<400> SEQUENCE: 2
tgaatttcct ccagcaacgg caa                                               23

<210> SEQ ID NO 3
<211> LENGTH: 26
<212> TYPE: DNA
<213> ORGANISM: Artificial Sequence
<220> FEATURE:
<223> OTHER INFORMATION: Synthetic forward primer

<400> SEQUENCE: 3
atgtgggatg ccaagaacat gatgtg                                            26

<210> SEQ ID NO 4
<211> LENGTH: 27
<212> TYPE: DNA
<213> ORGANISM: Artificial Sequence
<220> FEATURE:
<223> OTHER INFORMATION: Synthetic reverse primer

<400> SEQUENCE: 4
tccactccac aaagtaggaa gagttct                                           27
```

EXTRA-CHROMOSOMAL CIRCULAR DNA-MEDIATED ENGINEERING OF PLANT TRAITS

CROSS-REFERENCE TO RELATED APPLICATIONS

The present application claims the priority benefit of U.S. Provisional Patent Application Ser. No. 62/814,693, filed Mar. 6, 2019, entitled EXTRA-CHROMOSOMAL CIRCULAR DNA-MEDIATED ENGINEERING OF PLANT TRAITS, incorporated by reference in its entirety herein.

FEDERALLY SPONSORED RESEARCH OR DEVELOPMENT

This invention was made with government support under Contract No. 1338897 awarded by National Science Foundation. The government has certain rights in the invention.

SEQUENCE LISTING

The following application contains a sequence listing in computer readable format (CRF), submitted as a text file in ASCII format entitled "Sequence_Listing," created on Feb. 14, 2020, as 2 KB. The content of the CRF is hereby incorporated by reference.

BACKGROUND OF THE INVENTION

Field of the Invention

The present invention relates to novel techniques for producing improved plants using extra chromosomal circular plant DNA molecules.

Description of Related Art

Gene amplification has been observed in many bacteria and eukaryotes to overexpress specific genes in response to various selective pressures such as antibiotics, cytotoxic drugs, pesticides, herbicides and other stressful environmental conditions. Amplified gene copies are often found as part of autonomously replicating extra chromosomal circular DNA molecules (eccDNA) including double minutes (DMs). The eccDNAs have been widely observed in many drug-resistant and tumor cell lines. eccDNA vary in size ranging from a few hundred bases to kilobases megabases. eccDNA may be simple (oligomeric) in structure derived without any rearrangement from the corresponding chromosome, or complex eccDNAs with duplicated copies of the same gene. eccDNAs containing sequences from different chromosomal loci have also been reported, indicating that different mechanisms may drive eccDNA assembly and evolution.

Despite the lack of centromeres, eccDNAs can be transmitted to daughter cells by tethering of their chromatin body to the telomeric region of segregating chromosomes from anaphase to telophase. All reported cases of eccDNAs have been studied in cell lines; their genesis, behavior and inheritance has not been studied in soma and germ cells of living organisms.

Living organisms, including plants and insects, have also evolved resistance to xenobiotics compounds such as herbicides and insecticides via gene amplification. In all reported studies, amplified gene copies were located in specific chromosomes or multiple chromosomal regions, but not in the form of eccDNAs. Therefore, gene amplification in these living organisms is thought to have occurred by unequal recombination or in association with transposable elements.

*Amaranthus palmeri*, a crop weed, can develop herbicide resistance to glyphosate [N-(phosphonomethyl) glycine] by amplification of the 5-enolpyruvylshikimate-3-phosphate synthase (EPSPS) gene, the molecular target of glyphosate. However, biological questions regarding the source of the amplified EPSPS, the nature of the amplified DNA structures, and mechanisms responsible for maintaining this gene amplification in cells and their inheritance, persist.

SUMMARY

As described herein, amplified EPSPS gene copies conferring glyphosate-resistance (GR) in *A. palmeri* are present in the form of eccDNAs with various conformations. The eccDNAs are transmitted during cell division in mitosis and meiosis to the soma and germ cells and the progeny by a mechanism of tethering to mitotic and meiotic chromosomes. We propose that eccDNAs are one of the components of McClintock's postulated innate systems that can rapidly produce soma variation, amplify EPSPS genes in the sporophyte that are transmitted to germ cells and modulate rapid glyphosate resistance through genome plasticity and adaptive evolution. Despite the lack of centromeres, eccDNAs can be transmitted to daughter cells by tethering to the segregating chromosomes from anaphase to telophase. All reported cases of eccDNAs have been studied in cell lines. We have studied for the first time the genesis, behavior and inheritance of eccDNA in soma and germ cells of living organisms.

Described herein are methods of leveraging this new information by introducing heritable genetic traits into plants by transforming a plant cell with a stably incorporated artificial plant DNA construct carrying an agronomically useful trait. The approach includes introducing into the plant cell an extrachromosomal circular plant DNA comprising one or more exogenous genes conferring the agronomically useful trait when expressed in the plant cell, and/or one or more or endogenous genes conferring the agronomically useful trait when expressed in the plant cell in higher numbers than typically present in control plants. Advantageously, the extrachromosomal circular plant DNA associates or tethers itself to an endogenous chromosome in the plant cell such that it is stably maintained and replicated extrachromosomally in the plant cell.

The artificial plant DNA construct may be introduced by first culturing immature plant embryos to form callus tissue and transforming the tissue with the artificial plant DNA construct carrying an agronomically useful trait to yield the modified plant cells. The artificial plant DNA construct comprises an extrachromosomal circular plant DNA comprising one or more exogenous and/or endogenous genes conferring the agronomically useful trait when expressed in the plant tissue. Advantageously, the extrachromosomal circular plant DNA associates or tethers itself to an endogenous chromosome in the plant cell such that it is stably maintained and replicated extrachromosomally in the plant cell. The method further includes regenerating modified plants from the modified plant cells, wherein the trait is expressed in said modified plants. Moreover, the trait can be passed to progeny.

Aspects of the invention include recombinant plant cells produced by the inventive methods, as well as seeds from modified plants. Moreover, modified plants are also described herein. These plants comprise an extrachromosomal circular plant DNA comprising one or more exogenous and/or endogenous genes conferring an agronomically useful trait when expressed in the plant. As noted, the extrachromosomal circular plant DNA associates or tethers itself to an endogenous chromosome in the plant's cell such that it is stably maintained and replicated extrachromosomally in the plant cell.

Also described in herein are nucleic acid constructs comprising an extrachromosomal circular plant DNA comprising one or more exogenous genes conferring an agronomically useful trait when expressed in a plant, wherein the extrachromosomal circular plant DNA is operably linked to an element that associates or tethers itself to an endogenous chromosome in a plant cell to drive extrachromosomal expression and replication in a plant cell. Vectors comprising such nucleic acid constructions are also described herein. Such constructs and vectors can also be used to introduce endogenous genes into the plant in order to increase copy numbers of such genes to confer an agronomically useful trait when expressed in the plant in higher numbers than present in control plants.

Additional methods for introducing heritable genetic traits into plants include breeding plants having extrachromosomal circular plant DNA stably maintained and replicated extrachromosomally by association or tethering to an endogenous chromosome. In one aspect, the method comprises crossing a first parent plant with a second parent plant to produce progeny plants, wherein at least one of the first or second parent plant comprises an extrachromosomal circular plant DNA comprising one or more exogenous genes conferring an agronomically useful trait when expressed in the parent plant, wherein the extrachromosomal circular plant DNA associates or tethers itself to an endogenous chromosome in the plant's cells such that it is stably maintained and replicated extrachromosomally in the plant cells to be passed to progeny. The methods further comprise selecting for progeny plants having the extrachromosomal circular plant DNA comprising the one or more exogenous genes or higher numbers of endogenous genes conferring an agronomically useful trait stably maintained and replicated extrachromosomally in the progeny plant cell by association or tethering to an endogenous chromosome.

Additional methods for introducing heritable genetic traits into plants include breeding plants under one or more stressors to induce production of extrachromosomal circular plant DNA in the plant and selecting for progeny producing extrachromosomal circular plant DNA. In one or more embodiments, the selection is facilitated by detection of copy number variants, e.g., using a probe and/or detectable label, as an early maker of a desirable (or undesirable) trait even in soma cells. In one or more embodiments, copy number variants are detected via comparison with reference sequences.

Also described herein are methods of producing proteins in plants, and preferably high numbers of proteins. Methods include introducing a nucleic acid construct comprising an extrachromosomal circular plant DNA comprising one or more genes for a desired protein when expressed in a plant, wherein the extrachromosomal circular plant DNA is operably linked to an element that associates or tethers itself to an endogenous chromosome in a plant cell to drive extrachromosomal expression and replication in a plant cell. Advantageously, unlike constructs which become integrated into the host genome (e.g., bacterial plasmids), the extrachromosomal circular plant DNA is stably maintained and autonomously replicated extrachromosomally in the plant cell, such that it is capable of generating multiple copies (e.g., hundreds of copies) in each cell. Thus, the yield of produced protein can be much higher as compared to single genes integrated into the genome of each cell. This approach can be used to engineer plants to produce a variety of exogenous proteins not native to the host plant. Alternatively, it can be used to engineer plants to produce higher amounts of an endogenous protein. Thus, nucleic acid constructs and vectors can themselves be engineered to introduce a wide variety of coding sequences into the plant for protein production extrachromosomally.

Novel weed control methods are also described herein. Such methods comprise disrupting the association or tethering of extrachromosomal circular plant DNA with endogenous chromosomes in a weed, wherein the extrachromosomal circular plant DNA comprises one or more genes conferring herbicide resistance when expressed in the weed, such that the extrachromosomal circular plant DNA cannot be stably maintained and replicated extrachromosomally in the weed, thus rendering the weed and progeny susceptible to the herbicide. Methods also include converting resistant to susceptible plants by withholding herbicide treatment over the course of one or more progeny, wherein copy numbers of extrachromosomal circular plant DNA comprising one or more exogenous genes conferring resistance are decreased in the progeny over time.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
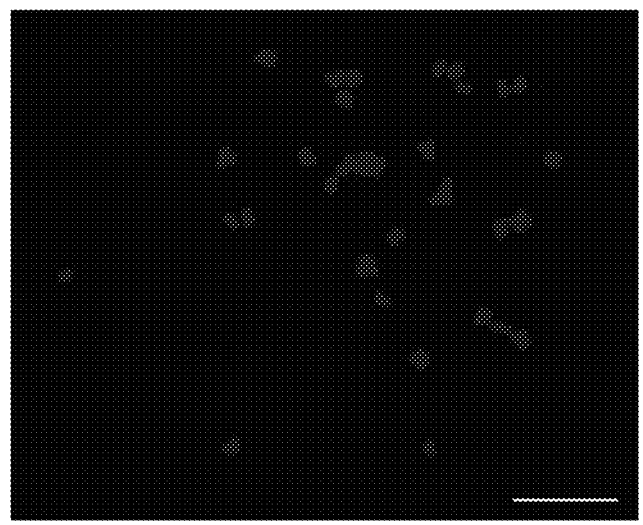
FIG. 1 shows images from FISH mapping of eccDNAs and EPSPS gene in mitotic metaphase chromosomes of root meristem cells of GR *A. palmeri* with 80 EPSPS copies: (A) mitotic metaphase chromosomes stained by DAPI; (B) eccDNAs showing green signals overlying all chromosomes except one (arrow denoting eccDNA not associated with metaphase chromosomes); (C) all eccDNAs seen in (B) carry EPSPS copies (red signal) with same arrowhead position.
Figure 1:
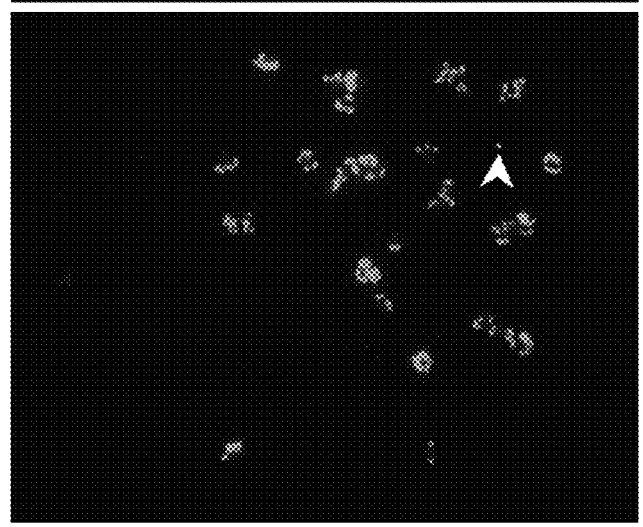
Figure 1:

Many traits including heat, drought, cold, hybrid seed fertility, herbicide tolerance, and the like, are controlled by gene copy number variation (CNV). This invention covers all the CNV-based traits that can be engineered by eccDNA-mediated gene amplification (or suppression of amplification), as illustrated in FIGS. 28A-E. Described herein are methods of introducing inheritable genetic traits into plants. Unless otherwise indicated by the context, references herein to a "plant" or "plants" includes tissues, organs, or parts thereof (e.g., leaves, stems, tubers), fruit, seeds, or cells thereof. The methods generally comprise transforming or modifying a plant cell with a stably incorporated artificial plant DNA construct carrying, e.g., a responder gene for CNV for an agronomically useful trait, such as drought tolerance, heat tolerance, cold tolerance, geographic adaptation, stalk strength, pathogen and pest resistance (virus, bacteria, fungal, nematode, insect, etc.), disease resistance, herbicide resistance, stress tolerance, moisture tolerance, salt tolerance, and combinations thereof. Useful traits also include those that improve plant performance, such as increased yield, stalk strength, seed weight, and the like. The methods comprise introducing into the plant cell an extrachromosomal circular plant DNA comprising one or more exogenous genes, which upon CNV, confer the agronomically useful trait when expressed in the plant cell.

As used herein, an "exogenous gene," is a gene not normally found in the host genome (the plant or cell to be modified) in a natural or wild type/control setting. Examples include genes originating (and isolated) from a different species than that of the host genome or from the same species but a different strain than that of the host genome, or modified sequences that differ from the native gene, as compared to its native expression. Two or more exogenous genes can be introduced via a single transformation event using either individual extrachromosomal circular plant DNAs, each comprising a single exogenous gene, or using a single extrachromosomal circular plant DNA incorporating two or more exogenous gene coding sequences.

Methods contemplated herein also involve introducing into the plant cell an extrachromosomal circular plant DNA comprising one or more endogenous genes conferring this agronomically useful trait when expressed in the plant cell in higher amounts than found in a control plant. In other words, the introduced "endogenous" gene is one that is normally expressed in the host plant species or strain (e.g., in a wild type or control setting), but in small amounts, e.g., as a single copy in each cell. In contrast, by using the extrachromosomal circular plant DNA as the vector for introducing the endogenous gene(s), multiple copies of the gene can be generated and expressed in the plant, increasing the expression of the gene as compared to a control plant and thus conferring the trait.

Accordingly, the term "extrachromosomal circular plant DNA" is distinguished from bacterial plasmids and refers to extrachromosomal circular DNA of plant origin which remains "extrachromosomal" and does not get incorporated into the host plant genome. In other words, the extrachromosomal circular plant DNA comprises, inter alia, autonomous replication sequences that facilitate its extrachromosomal replication and maintenance outside the chromosome(s) of the host plant. It will be appreciated that such a mechanism permits the generation of a plurality of copies of the introduced sequence in each cell, and in some cases, hundreds of copies of the sequence in each cell (in contrast to sequences integrated into the chromosome yielding only a single copy), such that whole plant traits can be affected by introduction of the extrachromosomal circular plant DNA. The technology can be used to increase copy number of endogenous sequence and translated proteins in the plant, or to introduce multiple copies of exogenous sequences and translated proteins in the plant.

Advantageously, the extrachromosomal circular plant DNA associates or tethers itself to an endogenous chromosome in the plant cell such that it is stably maintained and replicated extrachromosomally in the plant cell. In one or more embodiments, the extrachromosomal circular plant DNA has a chromatin body that is tethered to a telomeric region of segregating chromosomes from anaphase to telophase during replication in the plant cell. In one or more embodiments, the extrachromosomal circular plant DNA comprises cis acting sequences that recruit cellular transacting factors to mediate this chromosome association. In one or more embodiments, the extrachromosomal circular plant DNA lacks a centromere.

Plant expression vectors or transformation vectors comprising artificial plant DNA constructs are also contemplated herein. Nucleic acid constructs according to aspects of the invention will generally comprise an extrachromosomal circular plant DNA comprising one or more exogenous or endogenous genes conferring an agronomically useful trait when expressed in a plant, particularly in high copy numbers. The extrachromosomal circular plant DNA may also carry a responder gene, such as EPSPS, which in response to a stressor (e.g., glyphosate) can be used to select cells, tissues, and plants with high copies of the extrachromosomal circular plant DNA. In one or more embodiments, the construct or vectors comprise extrachromosomal circular plant DNA operably linked to one or more regulatory sequences for expression in a plant cell.

The expression vectors of the invention comprise extrachromosomal circular plant DNA in a form suitable for expression of the exogenous or endogenous gene in a host cell, which means that the expression vectors include one or more regulatory sequences, selected on the basis of the host cells to be used for expression. Within an expression vector, "operably linked" is intended to mean that the extrachromosomal circular plant DNA of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression desired, etc. Various techniques can be used to introduce the artificial DNA constructs into the plants, including leaf-rub inoculation, biolistic particle delivery system, microprojectile bombardment, viral infection, electroporation, liposomal delivery, and the like. The term "bombardment" with respect to transformation refers to the process of accelerating particles towards a target biological sample (e.g., cell, tissue, etc.) to effect wounding of the cell membrane of a cell in the target biological sample and/or entry of the particles into the target biological sample. In one or more embodiments, the methods comprise culturing immature plant embryos to form callus tissue or otherwise culturing plant tissue (e.g., leaf, cotyledon, or hypocotyl explants) on a suitable media (e.g., Murashige and Skoog (MS), or Chu (N6)), and transforming the tissue with an artificial plant DNA construct carrying the agronomically useful trait to yield modified plant cells by introducing into the tissue an extrachromosomal circular plant DNA comprising one or more exogenous or endogenous genes conferring the agronomically useful trait when expressed in the tissue.

Regardless of the technique, once the construct is introduced, is can be expressed in the cell such that the relevant gene product (i.e., protein) conferring the agronomically useful trait are produced in the transformed plant which then exhibits such trait(s). As noted, the extrachromosomal replication permits much higher copy numbers to be generated and thus, much higher yields of produced protein per cell as compared to traditional techniques. It will be appreciated that the technology can be used to generate a wide variety of desired proteins in the plant cell. The approach is not necessarily limited to expressly proteins conferring agronomically useful traits to the plant itself, but instead proteins which could be subsequently isolated from the cell or plant tissue for various applications.

Preferably, the extrachromosomal circular plant DNA is configured or operably linked to an element that associates or tethers itself to an endogenous chromosome in a plant cell transformed with the construct to drive extrachromosomal expression and replication in the plant cell. The nucleic acid construct can further comprise one or more reporter genes or selectable markers for identifying transformed cells, such as a reporter gene, e.g., EPSPS gene which in high copy number imparts resistance to glyphosate. Thus, this system allows for selection of cells, tissues, and plants with many copies of extrachromosomal circular plant DNA per cell including endogenous or exogenous gene(s). Methods of the invention can further include growing the modified cells on media, selecting for the marker, and isolating modified plant cells with the marker for subsequent use. Again, methods can also include isolating the produced protein from the modified plant cells and/or tissues for desired use.

In one or more embodiments, the method can comprise subjecting the plant cell to a stressor to identify a responder gene or element which, upon CNV via extrachromosomal circular plant DNA amplification, controls the agronomically useful trait, to thereby promote association or tethering of the extrachromosomal circular plant DNA to a correct position on the endogenous chromosome in the plant cell for stable maintenance and replication extrachromosomally in the plant cell. For example, the stressor could be an herbicide wherein the agronomically useful trait is herbicide resistance. Likewise, the stressor could be withholding of water, wherein the agronomically useful trait is drought tolerance. Other stressors include, without limitation, excessive heat, cold, pest exposure, disease, excessive moisture, salt, and any combinations thereof.

Modified plants can be regenerated using various techniques depending upon the plant species involved. In one or more embodiments, regeneration comprises inducing callus formation from the transformed tissue, and regeneration of shoots, followed by rooting of the shoots in soil or other appropriate rooting media to generate the whole plant, wherein the trait is expressed in the modified plants, and is importantly, inheritable by progeny plants, such that the trait is expressed in progeny from the modified plants. The technology is suitable with a variety of plants, including, without limitation, wheat, oat, barley, rice, maize, rye, millet, triticale, buckwheat, *quinoa*, sorghum, soybeans, beans, peas, alfalfa, tomato, cotton, tobacco, potato, sweet potatoes, cassava, yam, and citrus.

Additional methods of the invention comprise providing a first parent plant comprising an extrachromosomal circular plant DNA comprising one or more exogenous or endogenous genes conferring an agronomically useful trait when expressed in the parent plant, wherein the extrachromosomal circular plant DNA associates or tethers itself to an endogenous chromosome in the plant's cells such that it is stably maintained and replicated extrachromosomally in the plant cells. The first parent plant is crossed, e.g., through traditional plant breeding techniques, with a second parent plant to produce progeny plants. Progeny plants can then be selected which have the extrachromosomal circular plant DNA comprising the one or more exogenous or endogenous genes conferring an agronomically useful trait, wherein the extrachromosomal circular plant DNA associates or tethers itself to an endogenous chromosome in the progeny plant cell such that it is stably maintained and replicated extrachromosomally in the progeny plant cell. Embodiments of the invention further comprise subjecting the progeny plants to a stressor related to the agronomically useful trait, wherein exposure to the stressor leads to identification of responder gene via extrachromosomal circular plant DNA amplification or promotes association or tethering of the extrachromosomal circular plant DNA to a correct position on the endogenous chromosome in the progeny plants for stable maintenance and replication extrachromosomally in the plant cells to confer the agronomically useful trait.

Embodiments described herein also involve breeding plants under a stressor to induce production of extrachromosomal circular plant DNA containing a responder gene, followed by selecting for plants or cells containing the extrachromosomal circular plant DNA. In one or more embodiments, selection includes detecting plants or cells with high copy number variation as an early marker of successful induction of extrachromosomal circular plant DNA production. Reference sequences can be used to assist with identification. Once the target sequence is identified, various probes and/or labels can be developed to facilitate identification for the trait going forward to assist with breeding, such as by using fluorescence in situ hybridization (FISH) techniques or sequencing. For example, the technique could be used to develop salt tolerant wheat. The methods comprise growing a plurality of different wheat lines, particularly those collected from salty soil sources. The resulting germplasm from each line can then be subjected to the stressor (in this case salt stress), followed by selection of lines that have a responder gene via extrachromosomal circular plant DNA amplification. That is, the sequencing of control and tolerant plants will identify sequences of genes showing copy number variation. The location of such genes can then be ascertained to determine if it is present on extrachromosomal circular plant DNA. Thus, the method not only provides for selection of salt tolerance traits but also identifies the genes involved in salt tolerance.

The invention also concerns modified seeds, tissues, cells, and plants produced by the methods, and the progeny thereof. For example, modified plants are described herein which comprise an extrachromosomal circular plant DNA comprising one or more exogenous or endogenous genes conferring an agronomically useful trait when expressed in the plant. Advantageously, the extrachromosomal circular plant DNA associates or tethers itself to an endogenous chromosome in the plant's cells such that it is stably maintained and replicated extrachromosomally in the plant cells.

In one or more embodiments, modified plants according to the invention have a phenotype/morphology that is otherwise substantially similar to, and in some cases, nearly identical to wild-type plants of the same species. In other words, the techniques of the invention do not adversely affect the wild-type morphology or phenotype of the plant, such that the shape, size, and/or abundance of foliage and/or fruit/vegetable is substantially similar between the modified plants and wild-type plants. Plants are considered to be "substantially similar" herein if those skilled in the art have difficulty visually distinguishing between the modified plant and the control plant when grown under identical normal growing conditions. In contrast, when exposed to a stressor, modified plants according to the various embodiments of the invention, have significantly improved characteristics as compared to control plants grown under the same stressful conditions. For example, the modified plant may have one or more of the following improved characteristics: vigorous growth, abundant foliage, verdant foliage color, longer primary roots, yield, height, and/or shoot water potential, when grown in the presence of one or more stressors.

Embodiments of the invention can also be used as part of methods for weed control. The methods generally comprise disrupting the association or tethering of extrachromosomal circular plant DNA with endogenous chromosomes in a weed, and particularly extrachromosomal circular plant DNA comprising one or more genes conferring herbicide resistance when expressed in the weed, such that the extrachromosomal circular plant DNA cannot be stably maintained and replicated extrachromosomally in the weed. This renders the weed susceptible (again) to herbicide treatment.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

A "modified" plant, as used herein, refers to a genetically modified plant produced according to the inventive methods, into which an artificial DNA construct has been introduced extrachromosomally and/or in which the linkage between eccDNAs has been disrupted and/or in which copy number of endogenous eccDNAs have been artificially modified using the techniques described herein. Modified plants may be, but are not necessarily, transgenic (i.e., contain nucleic acid from a different species). In other words, modified plants may simply comprise a decrease or increase in copy numbers of eccDNAs as compared to endogenous copy numbers, more may comprise modified eccDNAs synthesized or derived from the same species of plant (but of a different strain or resistance state). That is, modified plants according to embodiments of the invention are not naturally occurring, but have been produced through human intervention, whether through artificial manipulation techniques or traditional breeding of progeny from modified parent plants. A "control" plant, as used in the present invention, refers to a plant used to compare against modified plants according to the invention for the purpose of identifying changes in the modified plant. The control plant is of the same species as the modified plant. In some cases, the control plant may be a wild-type (native) plant, although cultivars and genetically altered plants that otherwise have not be altered for viral resistance can also be used a reference for comparison. A "wild-type" plant is a plant that has not been genetically modified or treated in an experimental sense. A "wild-type" gene is one that has the characteristics of a gene isolated from a naturally occurring source. A "wild-type" gene product is one that has the characteristics of a gene product isolated from a naturally occurring source, whereas "modified" genes or gene products are those having modifications in sequence and/or functional properties (i.e., altered characteristics) when compared to the wild-type gene or gene product. Likewise, "genetically-modified" cells, tissues, seeds, plants etc. are those that have been altered to include a transgene and/or to change the expression, activity, function, or copy number of the target genes or gene products, as opposed to non-modified cells, tissues, etc. The term is synonymous with "genetically-engineered."

The term "vector" refers to nucleic acid molecules that transfer DNA segment(s) from one cell to another. The term includes recombinant DNA molecules containing a desired coding sequence(s) and appropriate nucleic acid sequences (e.g., promoters) necessary for the expression of the operably linked coding sequence in a particular host organism.

The term "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced The term "transform" is used herein to refer to the introduction of foreign DNA into cells. Transformation may be accomplished by a variety of means known to the art and described herein.

The term "isolated" when used in relation to a nucleic acid, refers to a nucleic acid sequence that is identified and separated from at least one contaminant nucleic acid with which it is ordinarily associated in its natural environment. That is, an isolated nucleic acid is one that is present in a form or setting that is different from that in which it is found in nature.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

To the extent the present description uses numerical ranges to quantify certain parameters relating to various embodiments of the invention, it should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Introduction

Glyphosate is a non-selective herbicide used around the globe for weed control in glyphosate resistant and non-crop situations. The extensive and exclusive use of glyphosate has led to the evolution of herbicide resistance in many crop weeds. The molecular target of glyphosate, 5-enopyruvly-shikimate-3-phosphate synthase (EPSPS) gene, upon amplification confers resistance and was first documented in glyphosate-resistant (GR) *Amaranthus palmeri*. We now report that amplified EPSPS copies in GR *A. palmeri* are present in the form of extra-chromosomal circular DNAs (eccDNAs) with various conformations. We discovered that eccDNAs are transmitted to the next generation by tethering to mitotic and meiotic chromosomes. These results represent a first report of novel extra-chromosomal structures that drive rapid adaptive evolution in higher organisms.

A 30 to more than 100-fold amplification of the 5-enolpyruvylshikimate-3-phosphate synthase (EPSPS) gene is associated with glyphosate resistance (GR) in *Amaranthus palmeri* (*A. palmeri*) populations. Initial reports suggested that EPSPS amplicon was at least 30 kb in length, and contained MITEs, which were postulated to disperse the amplicon to all the GR *A. palmeri* chromosomes at multiple sites. More recently, the length of the EPSPS amplicon was extended to 297 kb, and termed the "EPSPS cassette," by sequencing overlapping large-insert clones derived from a bacterial artificial chromosome (BAC) library. These clones flank the EPSPS gene, which was unique to GR *A. palmeri* across the USA, suggesting a single origin. Here we report that EPSPS cassette is in fact an extra chromosomal circular DNA carrying EPSPS gene, referred to herein as "eccDNA". We report on the dynamics of eccDNA structure, variation and behavior in mitotic and germ cells, possible modes of inheritance and discuss how they may trigger the plasticity of the GR response.

Results

Copy Number Variation (CNV) in the EPSPS Gene is Associated with Unique Chromosome Organization of the EPSPS Cassette.

Copy number variants are segments of DNA, typically 1 kilobase or larger, which present at a variable copy number in comparison with a reference genome. We identified glyphosate sensitive (GS) and GR isolates of *A. palmeri* with various EPSPS copy numbers ranging from 1 to 120 based on quantitative PCR (qPCR) assays (Table 1).

TABLE 1

EPSPS gene copy number in glyphosate-susceptible (GS) and -resistant (GR) *A. palmeri*. The relative EPSPS: β-tubulin gene copy number was adjusted to 1 for glyphosate-susceptible plants and the copy numbers for glyphosate-resistant plants shown here are relative to the susceptible plants

| Samples | EPSPS genomic copy number (β-tubulin as endogenous control) |
|---|---|
| Glyphosate-susceptible (GS) | 1*, 12*, 14, 18, 20 |
| Glyphosate-resistant (GR) | 62*, 78, 80*, 90, 120 |

Asterisks indicate the male plant that used for both mitotic- and meiotic chromosome analysis.
Some of female plants were also used in FISH.

Figure 20:
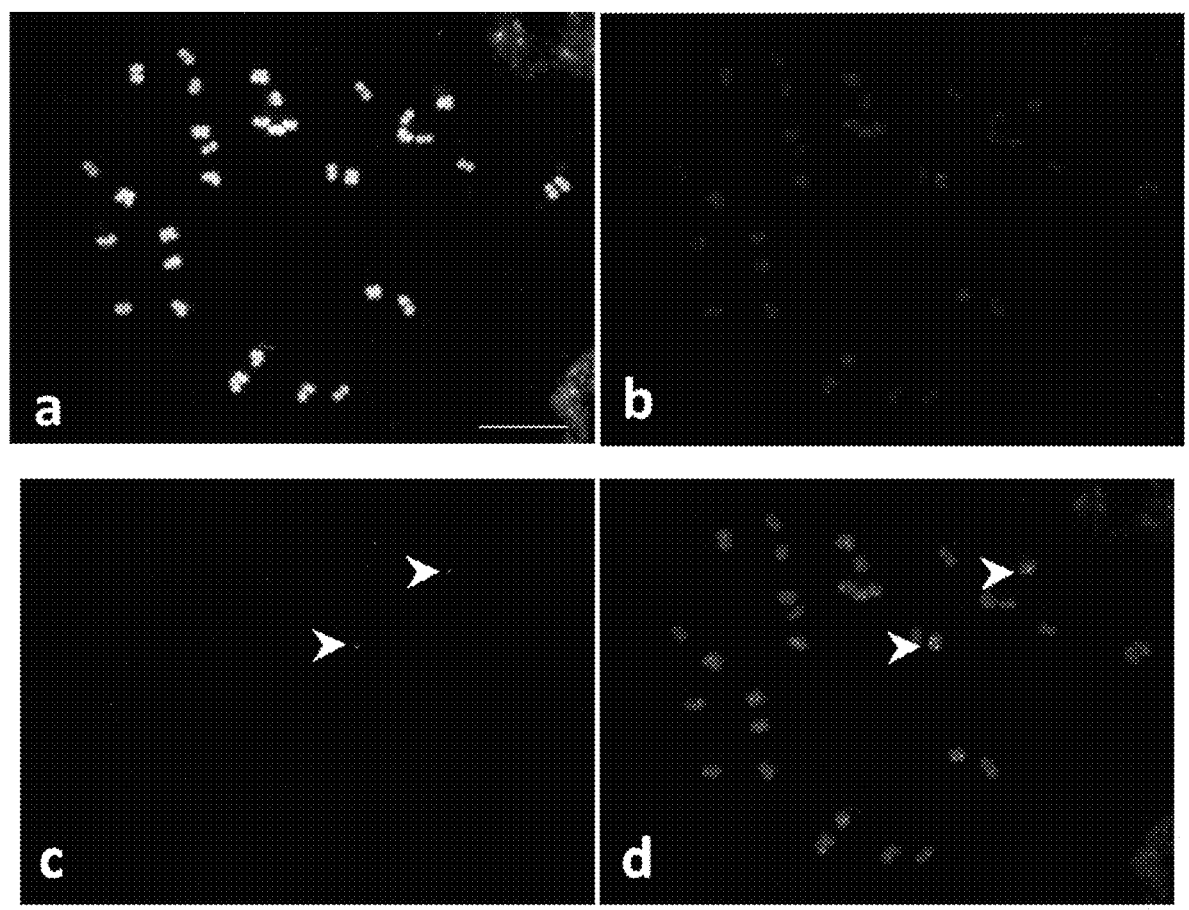
FIG. 20 shows images from two-color FISH mapping of the EPSPS gene (red signals) and eccDNA (green signals) on mitotic metaphase chromosomes, and pericentromeric location of the EPSPS gene in GS *A. palmeri* with one EPSPS gene copy; (Scale bar, 10 µm)

To study chromosome organization in relation to CNV of EPSPS gene, a DNA probe specific to the EPSPS gene and an EPSPS-containing BAC 22F22, or its flanking BACs, 5K07 and 1A02, were co-hybridized to chromosomes from several GS- and GR *A. palmeri* plants (FIGS. 1-4, & FIGS. 20-21). FISH using EPSPS gene probe on mitotic cells of GS *A. palmeri* with one copy of EPSPS revealed a tiny hybridization signal in the pericentromeric region of one pair of chromosomes (FIG. 20). FISH using BAC 22F22, in addition to tiny signal on one pair of chromosomes, also generated dispersed FISH sites on all chromosomes from the same GS plant (FIG. 20).

Figure 21:
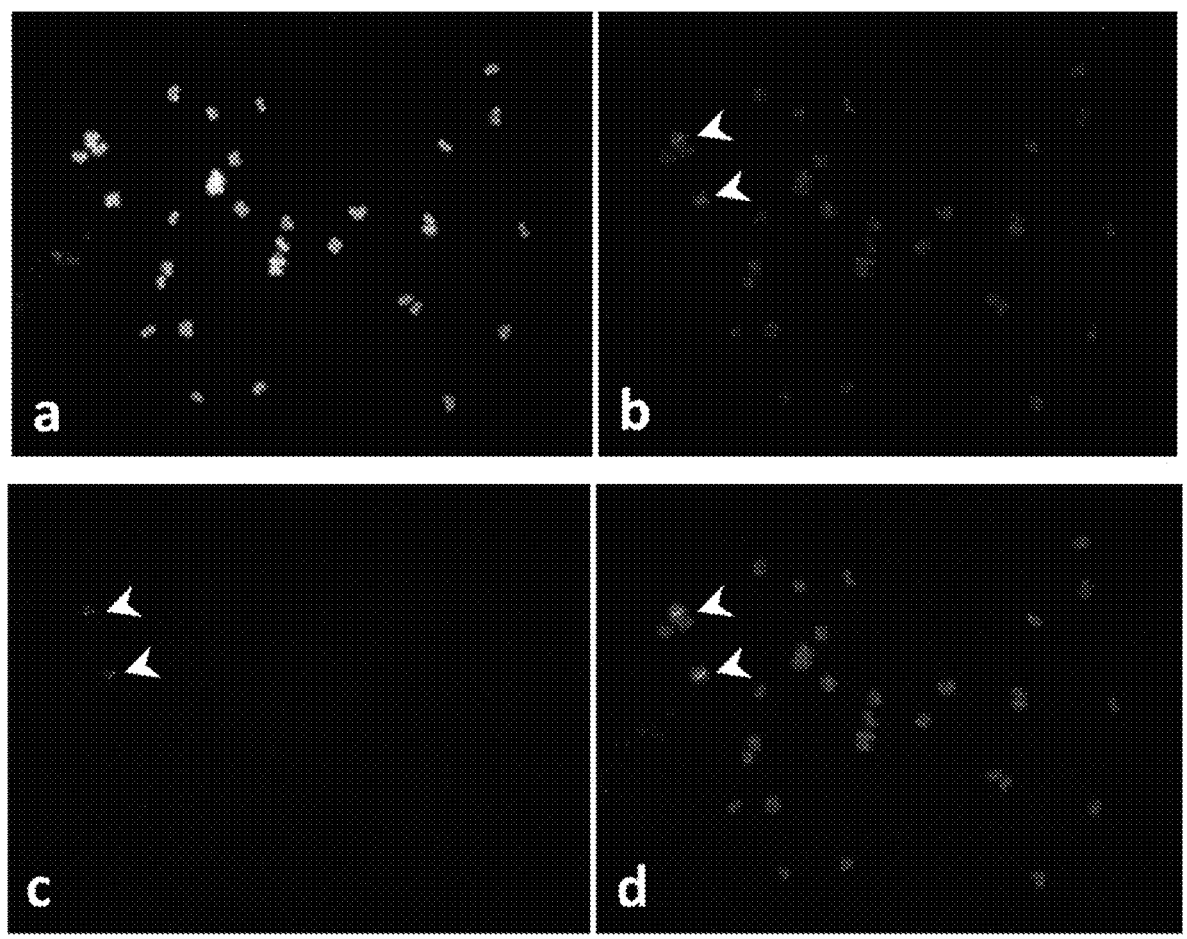
FIG. 21 shows images from two-color FISH mapping of the EPSPS gene (red signals) and eccDNA (green signals) on mitotic metaphase chromosomes, and pericentromeric location of amplified EPSPS genes in GS *A. palmeri* with 12 EPSPS copies, showing in comparison to FIG. 20, that in GS *A. palmeri*, eccDNA did not generate distinct hybridization signals, but significantly more intense signals (arrows) were detected at the amplified EPSPS gene locus in *A. palmeri* with 12 EPSPS copies. Arrows point to hybridization signals.
Figure 22:
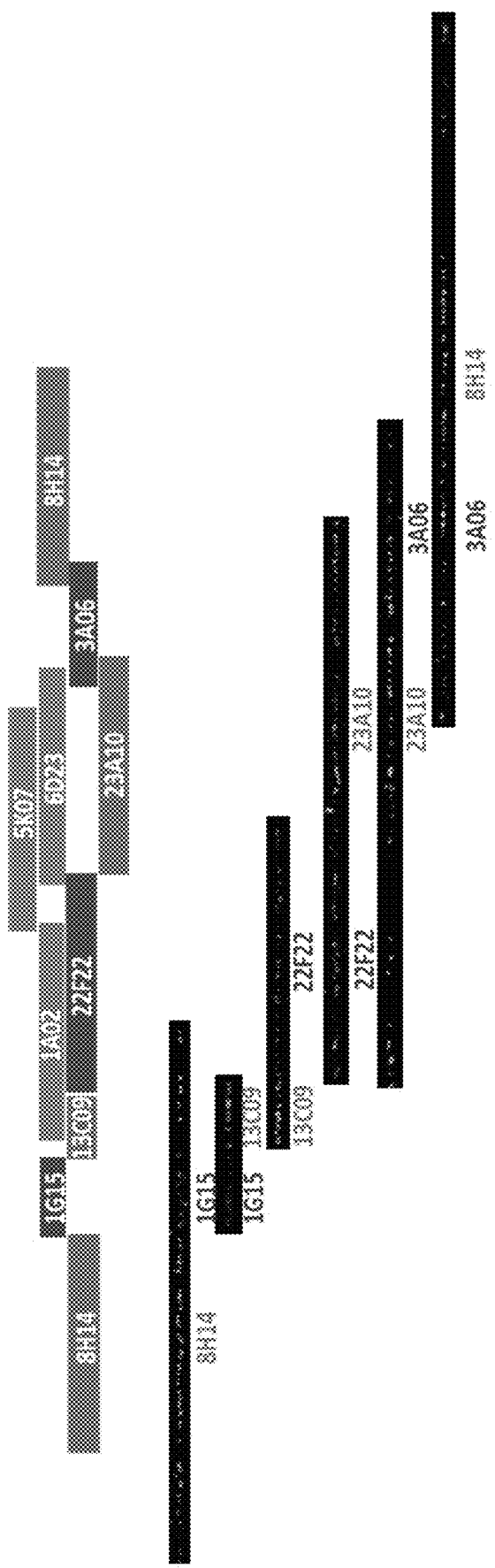
FIG. 22 is an illustration and imaging from BAC fiber-FISH analysis, showing validation of the ~400-kb BAC contig assembly using fiber-FISH, and BACs in pairs used in fiber-FISH to verify their orientation.

In an *A. palmeri* plant with 12 EPSPS copies, the EPSPS-FISH signals on one pair of chromosomes were brighter than those from GS plants with a single copy of EPSPS, indicating that the EPSPS gene in this plant was amplified near its original location (FIG. 21). The BAC 22F22-FISH hybridization signals were faint but dispersed over all the chromosomes except the significantly more intense hybridization signals at the amplified EPSPS gene locus (FIG. 21).

Figure 2:
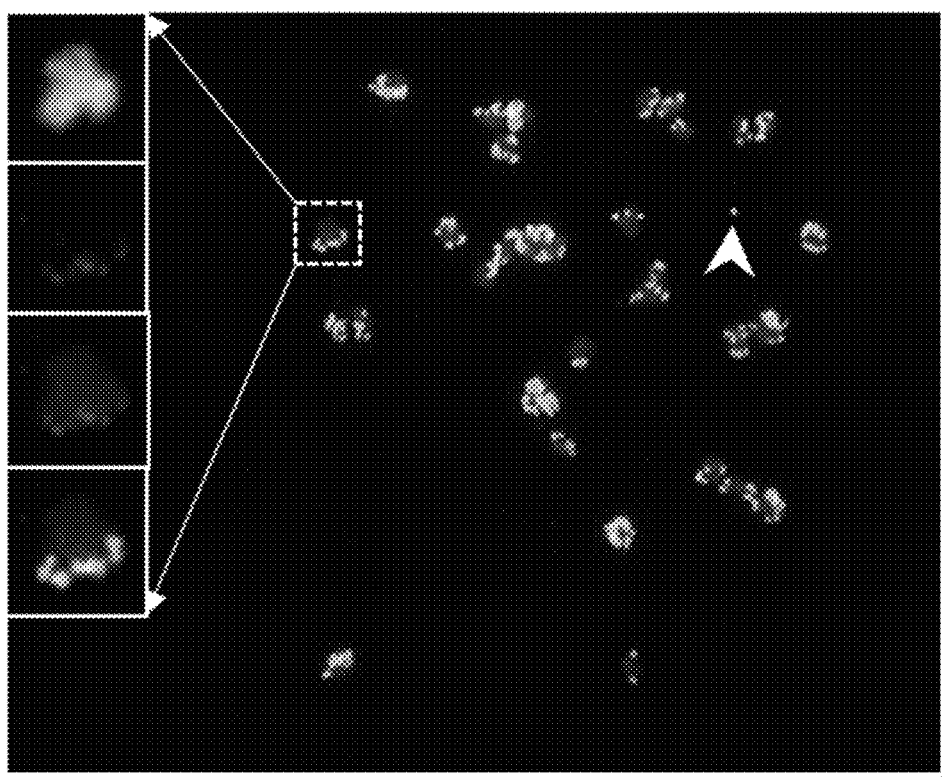
FIG. 2 is a merged image from FIG. 1 where the inset shows co-localization of eccDNA (green) and EPSPS signals (red) on the tip of a chromosome but are not part of the chromosome with arrow denoting eccDNA not associated with metaphase chromosomes.
Figure 3:
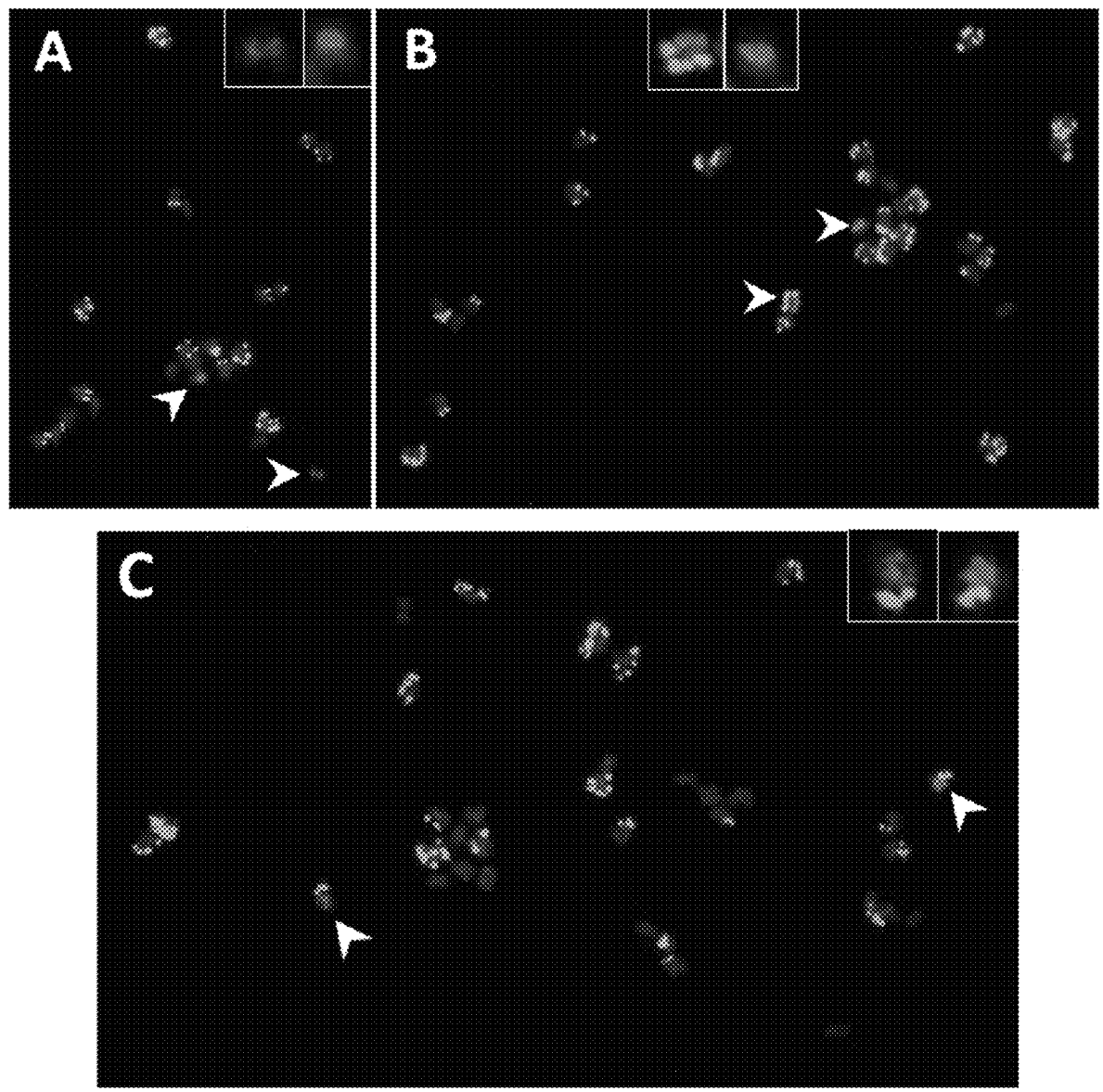
FIG. 3 shows (A) images of chromosome labeled with 5S rDNA (red/pink signals) free of eccDNAs; (B) another cell showed one marker chromosome free of signals but its homologue has eccDNA; and (C) both marker chromosomes have eccDNA signals, where the arrows point to 5S rDNA bearing chromosomes showing random distribution of eccDNAs in different cells.

In a GR *A. palmeri* plant with 80 EPSPS copies, EPSPS-FISH signals were detected on most chromosomes (FIGS. 1-4). However, the FISH signals appeared to be at the edges or outside of the condensed chromosomes (FIG. 1C & FIG. 2). Strong and distinct hybridization signals were generated using BAC 22F22 (FIG. 1B) and were co-localized with those of EPSPS signals (FIG. 2). Hybridization signals not associated with chromosomes were often observed in different metaphase cells of GR *A. palmeri* plants (arrows in FIG. 1B-C & FIG. 2). These data indicated that these structures were probably part of the EPSPS cassette reported by Molin et al. ((2017) The unique genomic landscape surrounding the EPSPS gene in glyphosate resistant *Amaranthus palmeri*: a repetitive path to resistance. BMC Genomics 18:91.) and we began studies on the structure of the cassette using FISH on extended DNA fibers.

EPSPS Cassette is an eccDNA Displaying Unique Structural Polymorphisms.

Figure 5:
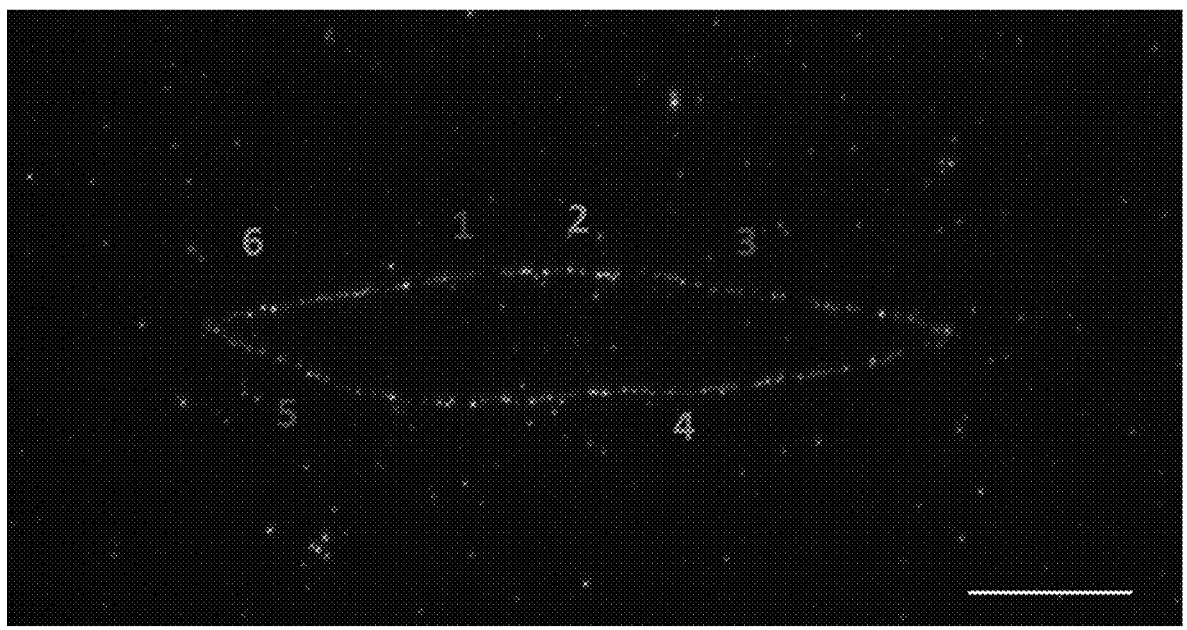
FIG. 5 is a Fiber-FISH image of a circular form of eccDNA in GR *A. palmeri* with 80 EPSPS copies.
Figure 23:
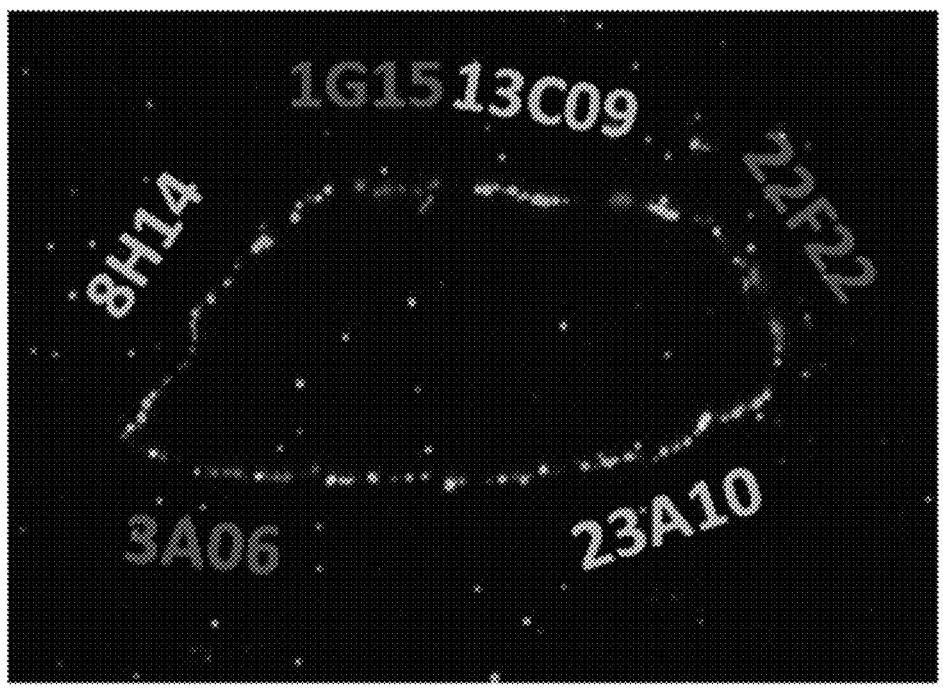
FIG. 23 is an image from pooling the six BACs and used with the probe in fiber-FISH to visualize the wild-type circular structure of eccDNA.

Molin et al. first reported the EPSPS cassette, which is 297 kb in length consisting of seven overlapping BACs. Further selection, by sequencing of two additional BACs revealed overlapping sequence of the free ends indicating a potentially circular orientation of EPSPS cassette. Six BACs associated with the EPSPS cassette were used in fiber-FISH mapping. These BACs were grouped into two pools, and they were labeled with alternate green/red colors based on their location in the EPSPS cassette (FIG. S2). Surprisingly, we found that approximately 50.2% of fibers are in circular form, indicating that the EPSPS cassette is in fact an eccDNA (FIG. 5, FIG. 23 and Table 2).

TABLE 2

Frequency of different structure polymorphisms of eccDNAs detected by fiber-FISH

| Structure | Circular | Linear | Dimeric circular | Dimeric linear | Atypical* |
|---|---|---|---|---|---|
| # of observations | 564 | 245 | 133 | 90 | 92 |
| Frequency, % | 50.2 | 21.8 | 11.8 | 8.0 | 8.2 |

*Fiber-FISH patterns that cannot be discriminated from other four types

Figure 6:
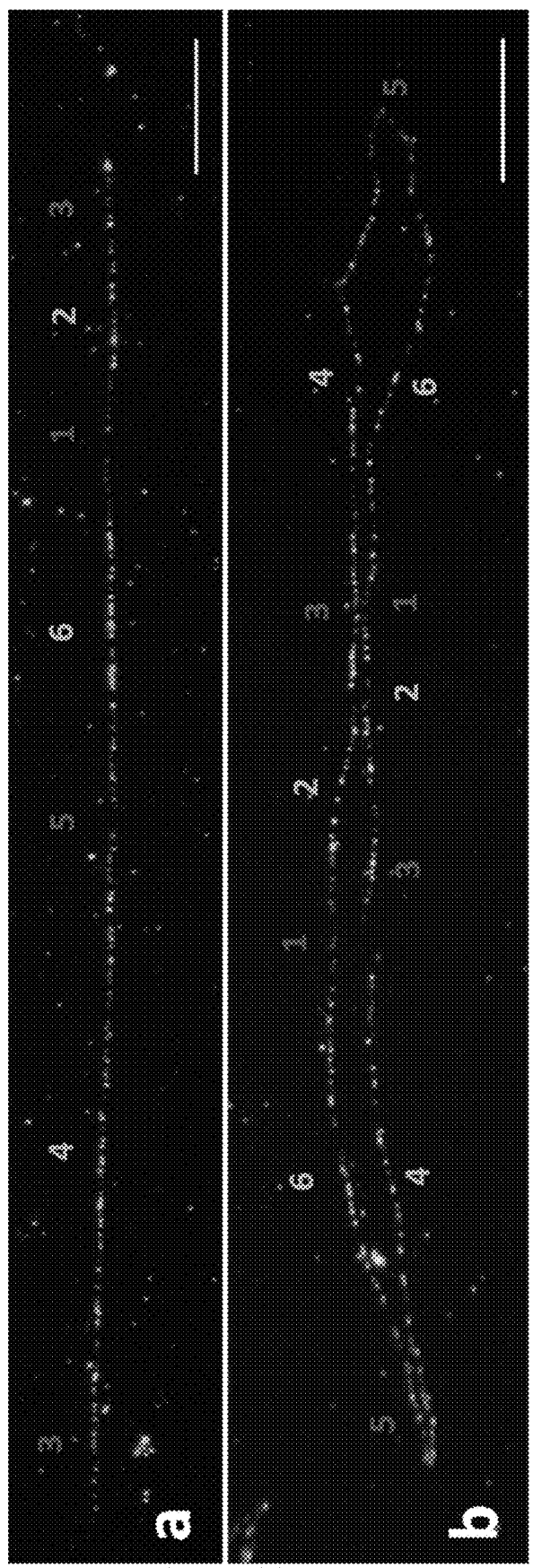
FIG. 6 shows (a) a Fiber-FISH image of a linear form of eccDNA in GR *A. palmeri* with 80 EPSPS copies; and (b) a Fiber-FISH image of a dimerized circular form of eccDNA with head-to-tail tandem orientation in GR *A. palmeri* with 80 EPSPS copies, where the numbers reference bacterial artificial chromosomes used: #1, BAC 01G15; #2, BAC 13C09; #3, BAC 22F22; #4, BAC 23A10; #5, BAC 03A06; #6, BAC 08H14; (Scale bar, 10 µm.)

Based on the proportion of red and green signal tracks in circular molecules, we consider these eccDNAs to be intact and the wild type form (FIG. 5). The microscopic size of circular form of these eccDNAs varied from ~30 μm to ~200 μm, which might be due to the variation of DNA fiber extension in the experiments. Therefore, we were unable to use the microscopic measurement data in classifying the eccDNA types. Instead we scored eccDNAs for structural polymorphisms based on circular or linear structure and the number and proportion of red and green signals. In the circular DNA class, another 11.8% were determined to be dimerized circular form of wild type eccDNA with head-to-tail tandem duplication (hereafter dimeric eccDNA) (FIG. 6).

Figure 7:
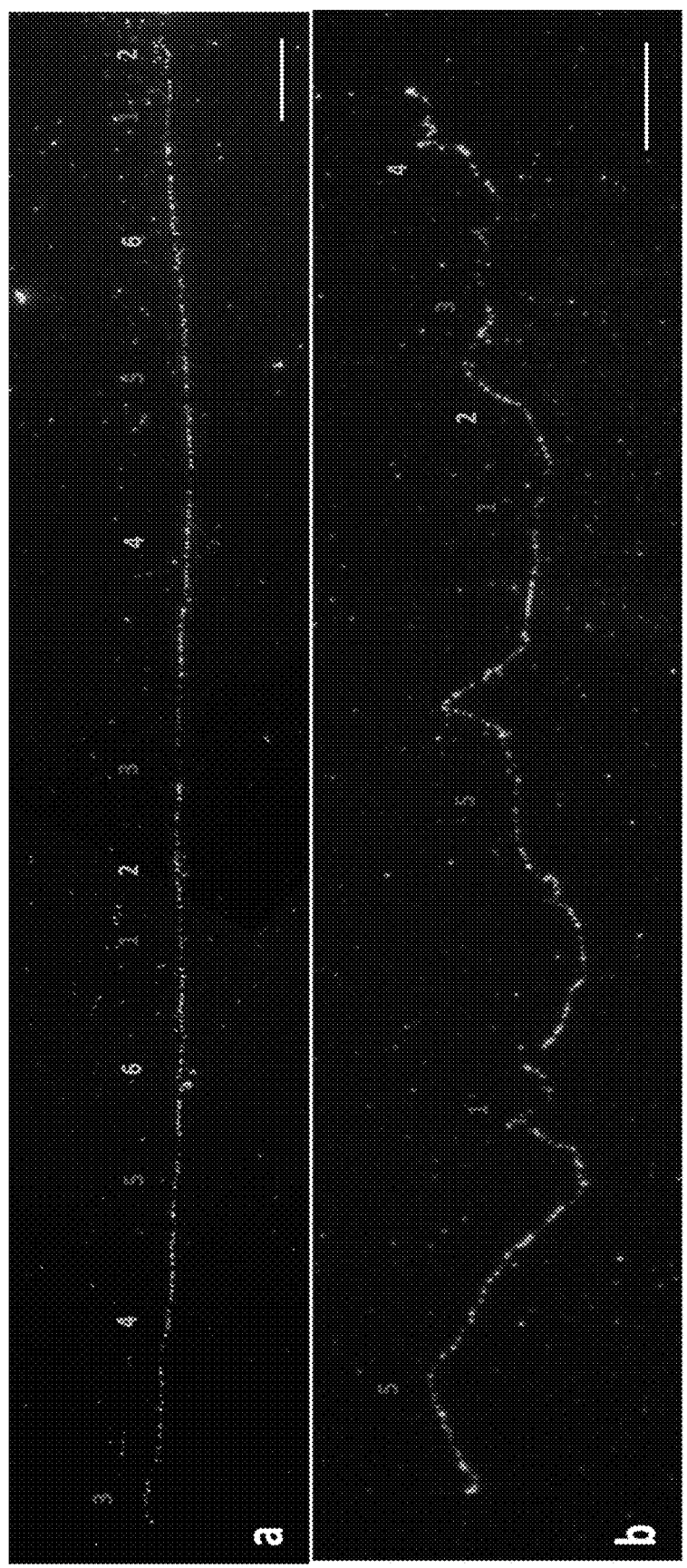
FIG. 7 shows (a) a Fiber-FISH image of a linear form of eccDNA with head-to-tail dimer in GR *A. palmeri* with 80 EPSPS copies; and (b) a Fiber-FISH image of an atypical fiber representing structural changes in GR *A. palmeri* with 80 EPSPS copies, where the numbers reference bacterial artificial chromosomes used: #1, BAC 01G15; #2, BAC 13C09; #3, BAC 22F22; #4, BAC 23A10; #5, BAC 03A06; #6, BAC 08H14; (Scale bar, 10 µm.)
Figure 8:
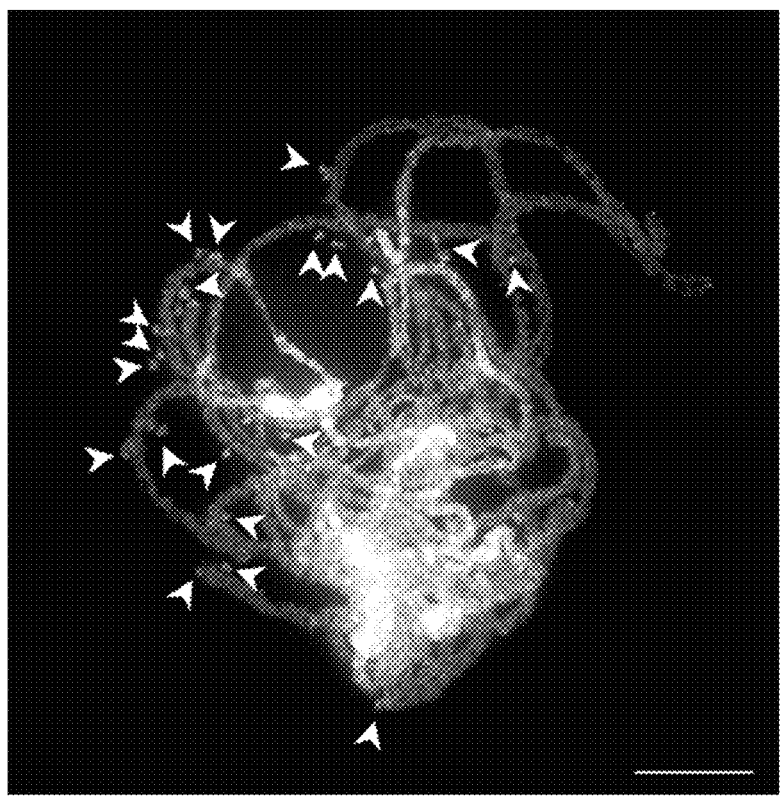
FIG. 8 is an image of a DAPI-stained pachytene chromosome showing eccDNAs lying outside the pachytene chromosomes (arrows); (Scale bar, 10 µm.)
Figure 9:
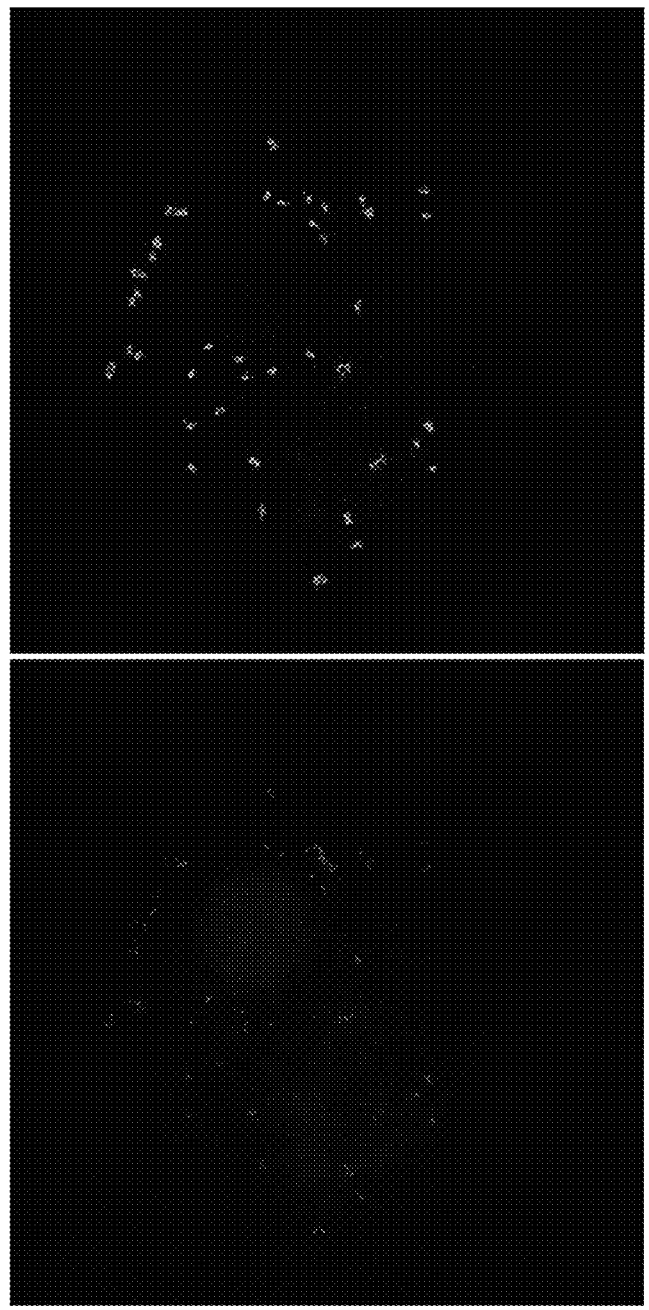
FIG. 9 shows images from FISH mapping of (A) eccDNA (green signals) and (B) EPSPS gene (red signals) on meiotic pachytene chromosomes of GR *A. palmeri* with 80 EPSPS copies and FISH signals with eccDNA and EPSPS gene probes.
Figure 24:
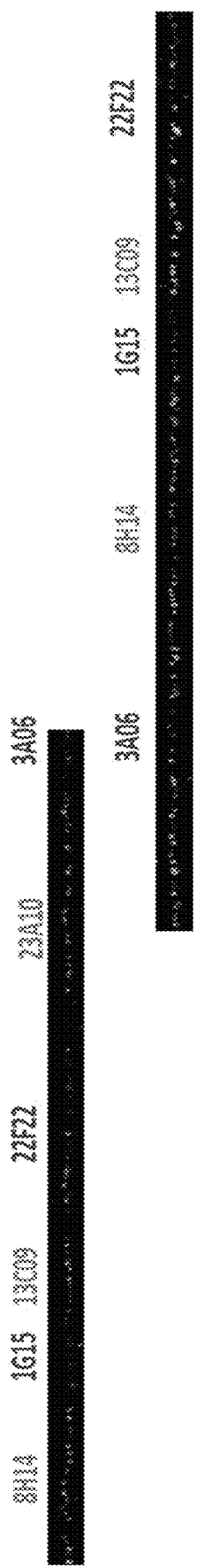
FIG. 24 is an image from pooling the six BACs and used with the probe in fiber-FISH to visualize the polymorphic linear structure of eccDNA.

The remaining 38% of the eccDNA showed linear structure (Table 2). Linearized fibers with different breakpoints but similar in composition to wild type eccDNA were the most frequent (21.8%) class (FIG. 6 and FIG. 24). Linear form of dimeric eccDNAs were also detected (8.0%) (FIG. 7). We also detected atypical fibers where the hybridization patterns deviated from the expected FISH patterns in 8.2% of the total fibers analyzed (FIG. 7). Overall, our results demonstrated that ~50% of eccDNAs of GR *A. palmeri* were structurally diverged due to duplication and deletion events (Table 2).

EccDNAs Display Copy Number Variation and Random Chromosome Associations in Soma Cells of GR *A. palmeri*.

Figure 4:
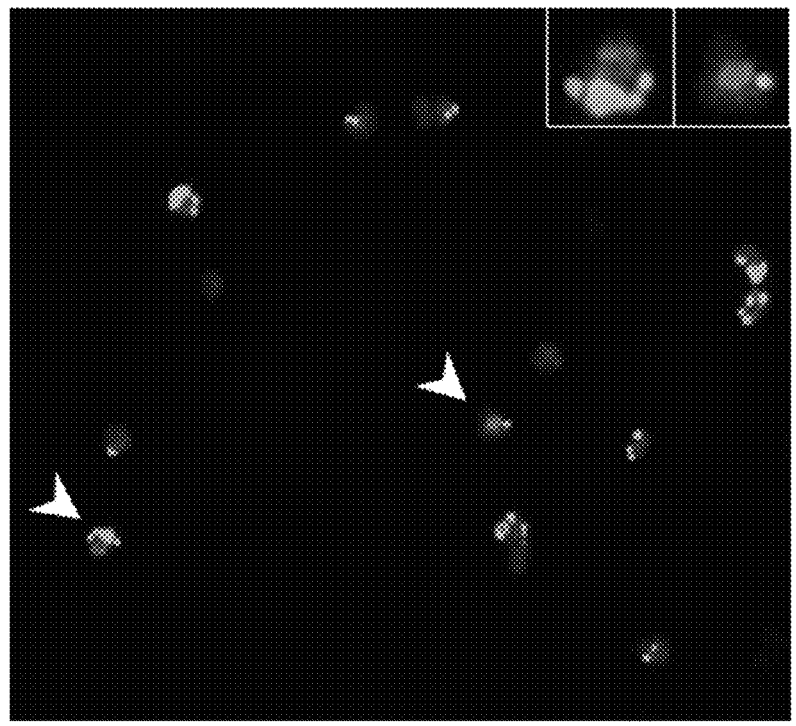
FIG. 4 is an image showing copy number variation of eccDNA signals among the two marker chromosomes, where the arrows point to 5S rDNA bearing chromosomes showing random distribution of eccDNAs in different cells.

The GR *A. palmeri* plants with 80 EPSPS copies as determined by qPCR displayed surprising copy number variation in soma cells as revealed by FISH. The hybridization patterns of the eccDNAs on metaphase cells varied from cell to cell in the same plant. To determine whether the hybridization patterns of metaphase chromosomes were random, a 5S rDNA probe was used in FISH, which showed hybridization signals on one chromosome pair of *A. palmeri*. We observed four different patterns of the eccDNA signals on 5S rDNA labeled homologous chromosome pair in different cells (n=24) from a single root tip meristem: i) both chromosomes were without eccDNA signals (16.7%) (FIG. 3A), ii) one of the two chromosomes was without eccDNA signal (25%) (FIG. 3B), iii) both chromosomes had similar signal intensity (33.3%) (FIG. 3C) and iv) the two chromosomes varied in signal intensity (25%) (FIG. 4). We conclude from these data that most of the eccDNAs are extra chromosomal elements that are randomly anchored to the chromosomes at mitotic metaphases.

EccDNAs Display Unique Behavior and a Chromosome Tethering Mechanism for Inclusion in Daughter Cells During Meiosis.

Figure 10:
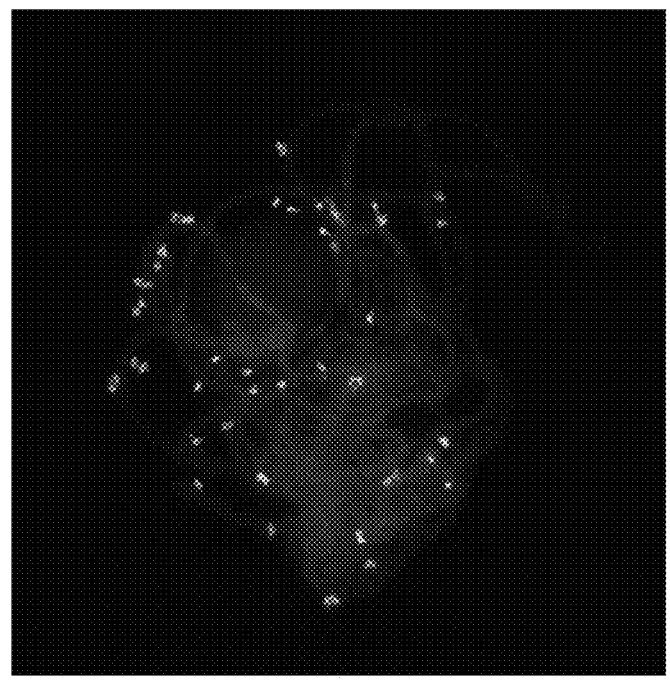
FIG. 10 is an image of co-localization of eccDNA and EPSPS probes to eccDNAs.
Figure 11:
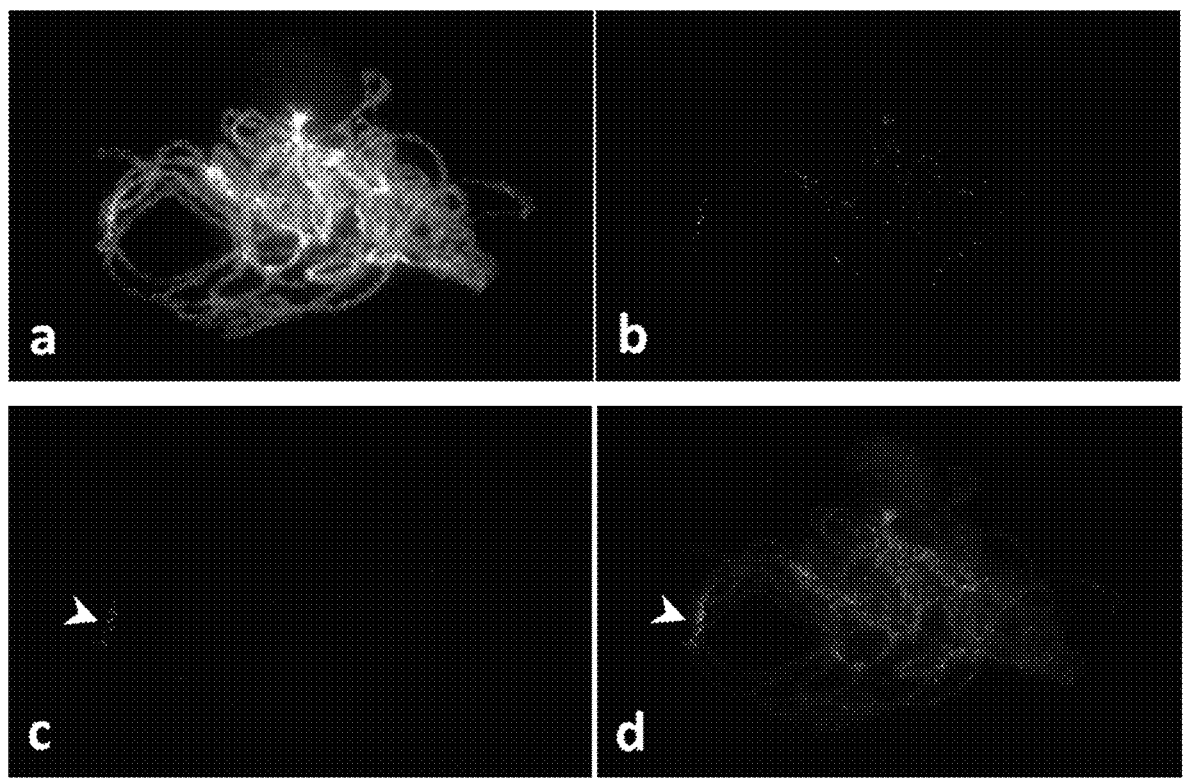
FIG. 11 shows images of DAPI-stained pachytene chromosome of GS *A. palmeri* with 12 EPSPS copies showing (a) no eccDNAs; (b) no signal with eccDNA probe; (c & d) amplified EPSPS gene signal in the pericentromeric region of one chromosome pair (arrows)

We analyzed distribution of eccDNAs in meiotic pachytene chromosomes of GS- and GR *A. palmeri* plants (FIGS. 8-11). As expected, the eccDNAs were not observed in GS *A. palmeri* plants with 1-12 EPSPS copies (FIG. 11a-d). However, DAPI (4',6-diamidino-2-phenylindole)-stained pachytene chromosome of the GR *A. palmeri* revealed numerous eccDNAs outside of the chromosome axis (arrows in FIG. 8) indicating that eccDNAs were not integrated into the chromosomes. The BAC 22F22 and EPSPS gene signals were colocalized (FIGS. 9A-B & 10).

Figure 12:
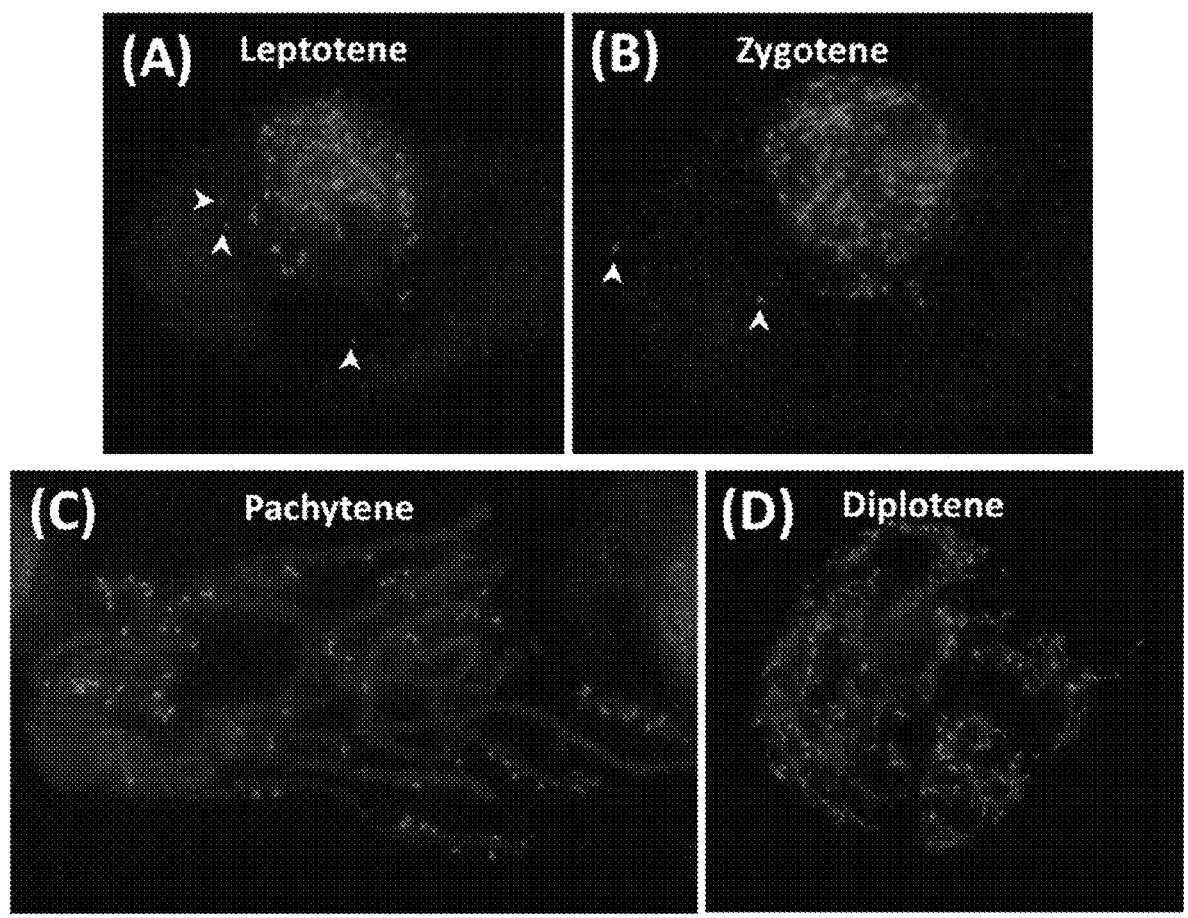
FIG. 12 shows images evidencing the distribution of eccDNAs (red signals) on meiotic chromosomes in microsporocytes of GR *A. palmeri* during progression from leptotene stage of meiosis I through diplotene as detected by FISH (arrows point to the eccDNAs that are not associated with chromosomes)
Figure 13:
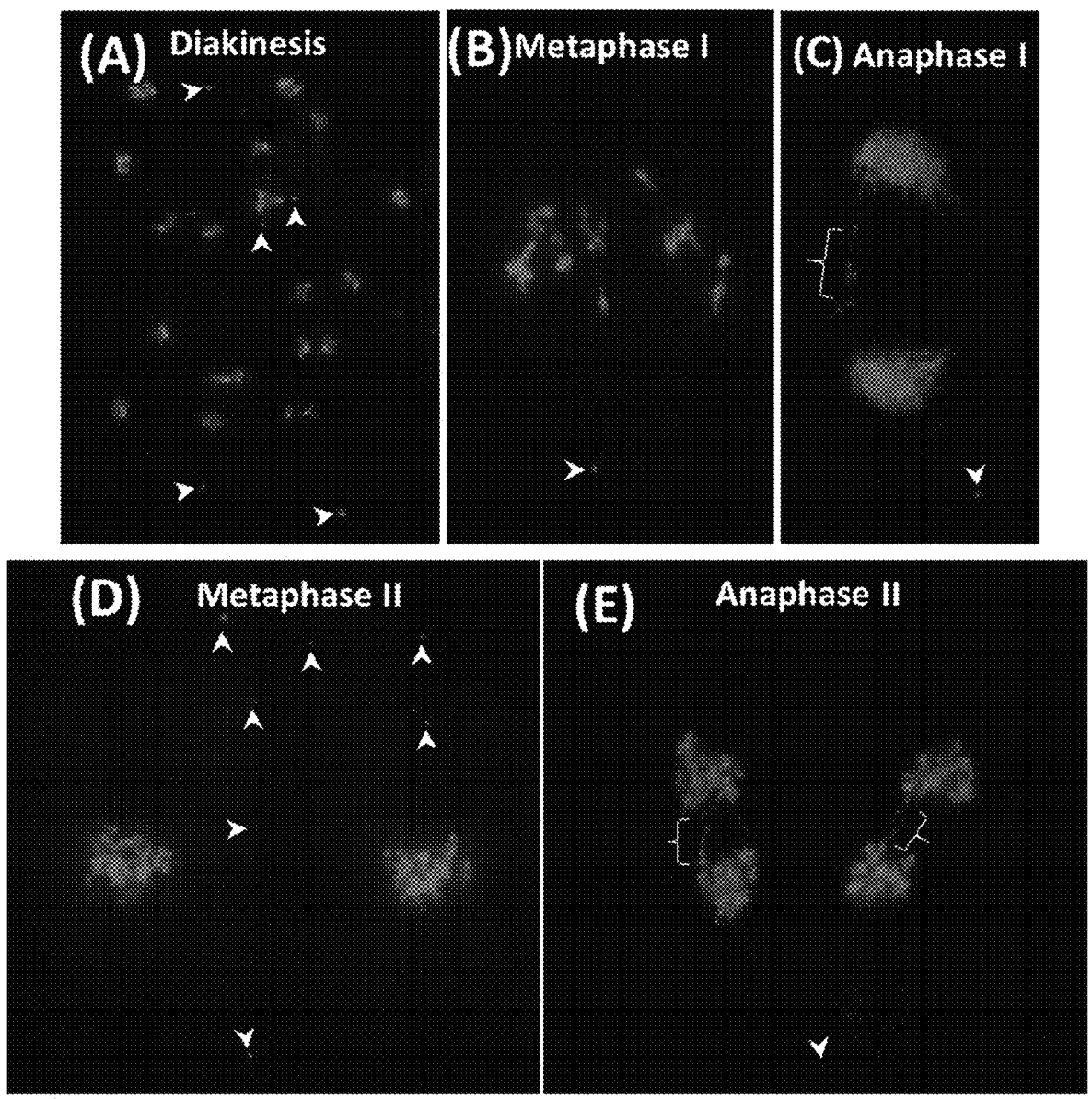
FIG. 13 shows images evidencing the distribution of eccDNAs (red signals) on meiotic chromosomes in microsporocytes of GR *A. palmeri* during progression from diakinesis through anaphase of meiosis II as detected by FISH (arrows point to the eccDNAs that are not associated with chromosomes, brackets represent the lagging eccDNAs associated with chromatin bridges at anaphase to telophase stages)
Figure 14:
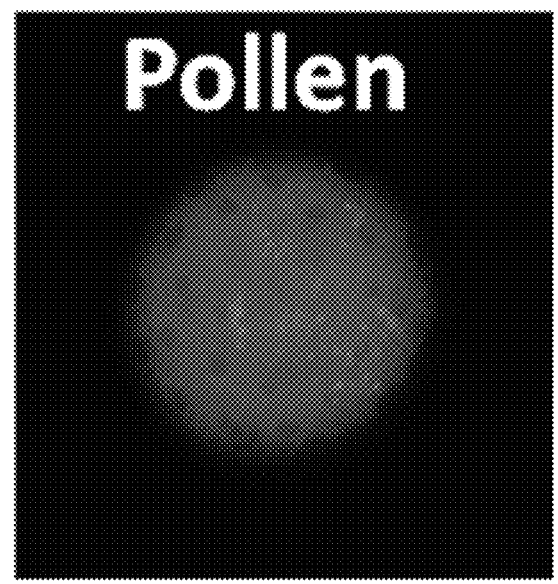
FIG. 14 is an image of pollen evidencing the distribution of eccDNAs (red signals) detected by FISH (arrows point to the eccDNAs that are not associated with chromosomes)

To further study this apparent tethering of the eccDNAs to chromosomes during cell division, we analyzed eccDNA behavior during all stages of meiosis I and II from leptotene to telophase II and also in immature pollen grains (FIGS. 12-14). Numerous eccDNAs can be seen associated with leptotene and zygotene chromosomes and a few are lying in the cytoplasm (arrows in FIG. 12A-B). At pachytene stage, homologous chromosomes are fully paired. If eccDNAs were integrated into the chromosomes, then double signals will be observed but most signals were not double but instead single or in clumps and lying next to the chromosomes (FIG. 12C). Moreover, random and variable association of eccDNAs to different chromosomes was seen in well-spread chromosomes at pachytene (FIG. 12C), diplotene (FIG. 12D), diakinesis (FIG. 13A) and metaphase stages (FIG. 13B). The association of eccDNAs to laggard and stretched chromosomes was clearly observed at anaphase I (FIG. 13C) and anaphase II (FIG. 13E). By metaphase II, a few eccDNA were seen lying away from the chromosomes in the cytoplasm (FIG. 13D). Pollen from GR plants also showed eccDNA signals indicating their transmission to the gametophyte (FIG. 14).

EccDNAs are Sexually Transmitted to Progeny Plants and Display Dramatic Copy Number Variation in Soma Cells.

Our meiotic chromosome study indicated the possibility of transmission of the eccDNAs to the offspring by a chromosome tethering mechanism. To study the sexual transmission, we made crosses between a female GSA. *palmeri* plant lacking eccDNAs and a male GR *A. palmeri* plant carrying the eccDNAs and vice versa. Ten $F_1$ plants from each reciprocal cross were randomly selected for qPCR and FISH analysis (FIGS. 15-19 & 25-26). FISH analyses of root tip cells in these 20 $F_1$ plants showed that all the plants had positive signals associated with their mitotic metaphase chromosomes, indicating the transmission of eccDNAs to the offspring.

Figure 15:
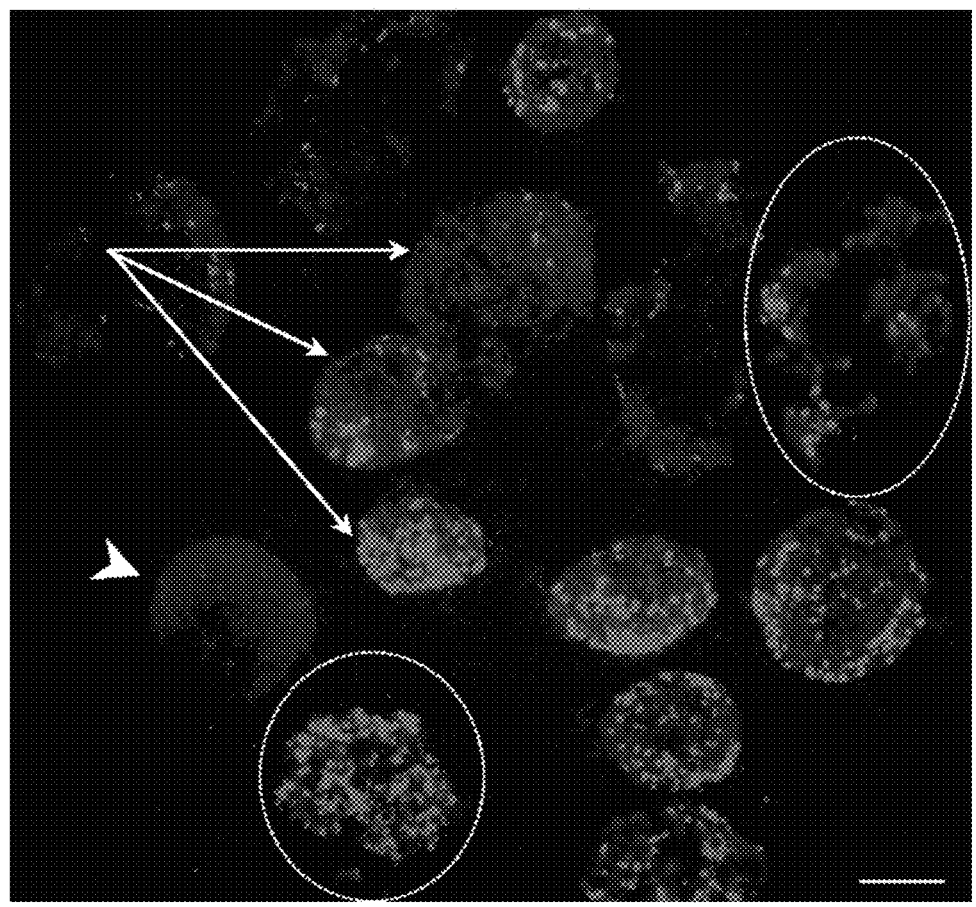
FIG. 15 is an image evidencing inheritance and soma cell heterogeneity of eccDNAs and EPSPS copy number in $F_1$ plants of GS *A. palmeri* x GR *A. palmeri* including cells lacking eccDNAs (arrows) in a single root tip meristem, with variable number of eccDNA FISH signals (red) in interphase and prometaphase stages (circles)
Figure 16:
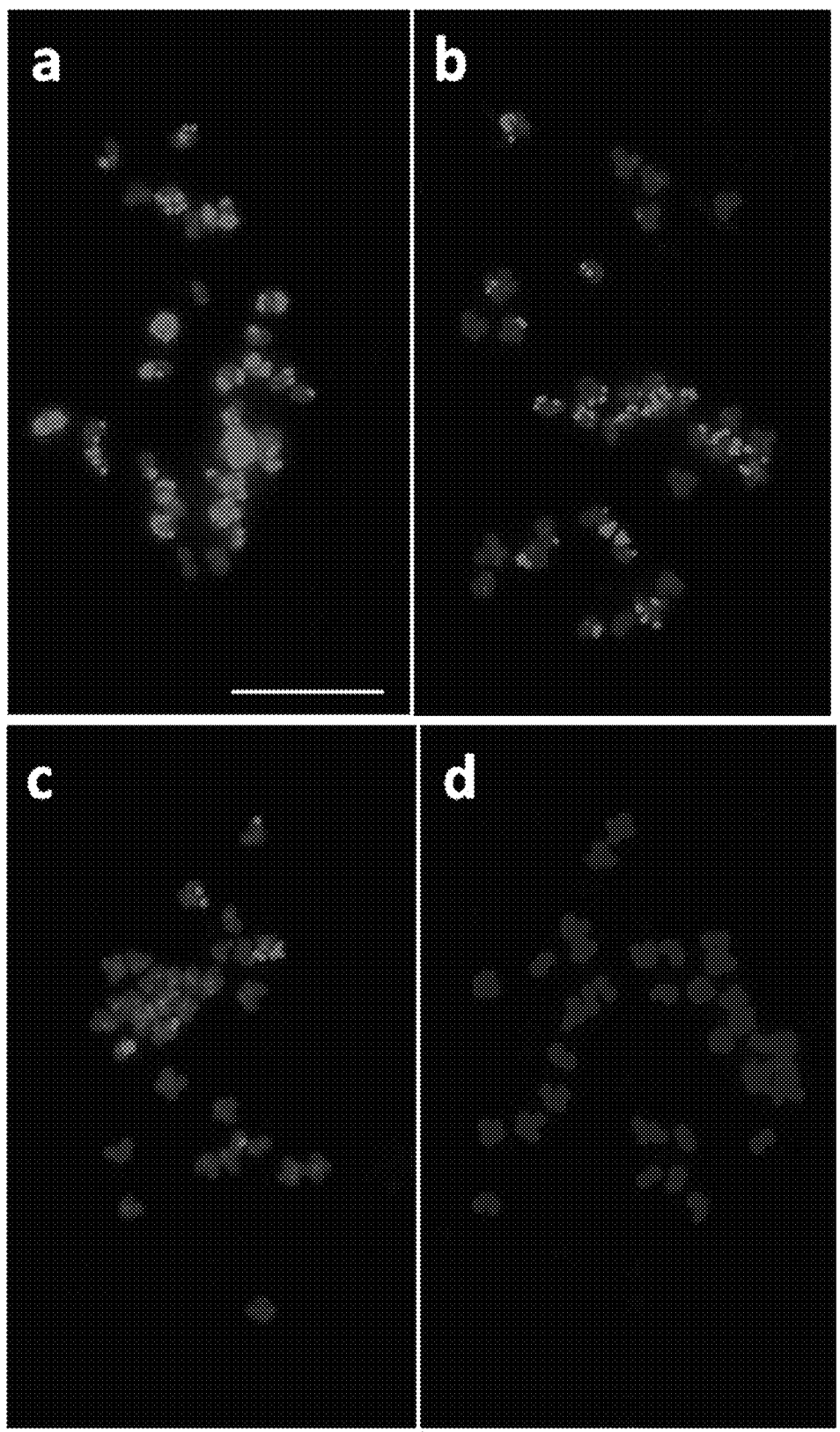
FIG. 16 shows images (a-d) of different metaphase cells from FIG. 15 showing variable number of eccDNAs including no eccDNAs.
Figure 17:
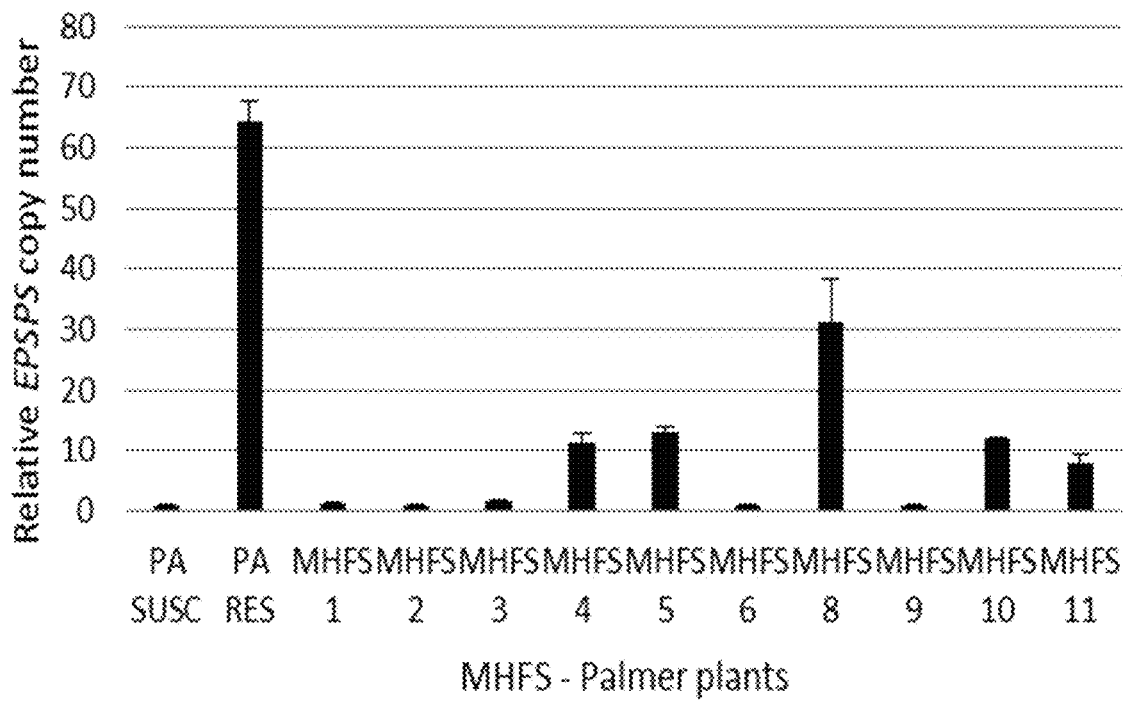
FIG. 17 is a graph showing the average EPSPS copy number of $F_1$ plants and the controls, the Y axis represents the relative β tubulin: EPSPS gene copy number.
Figure 25:
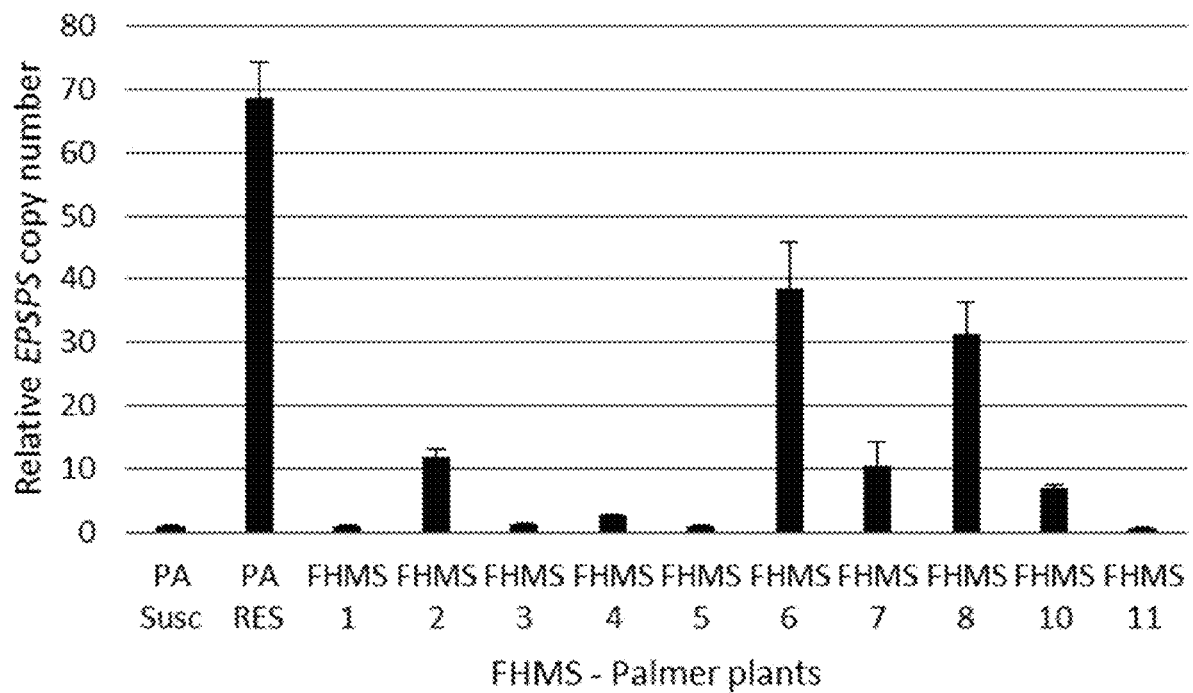
FIG. 25 is a graph showing EPSPS copy number of F1 progeny derived from male GS x female GR *A. palmeri*. Palmer amaranth glyphosate susceptible [PA SUSC (GS)] and Palmer amaranth glyphosate resistant [PA RES (GR)] were used as controls. The y axis represents the relative β-tubulin/EPSPS gene copy number.
Figure 26:
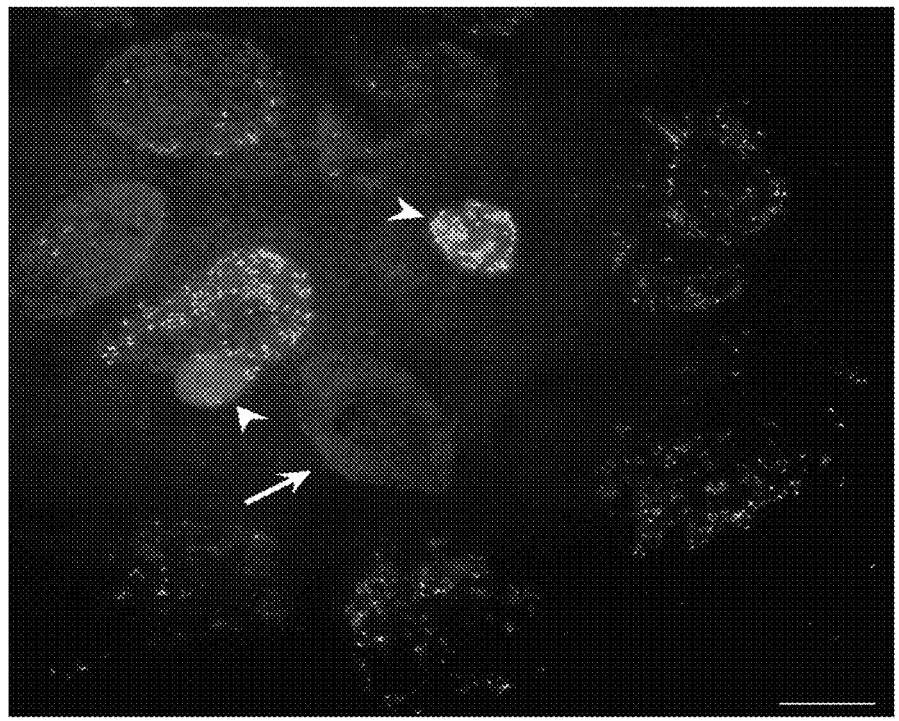
FIG. 26 is an image of FISH mapping of eccDNA (red signals) on mitotic metaphase chromosomes and interphase nuclei in plant FHMS 6. Similar FISH patterns were detected on the metaphase cell spreads in all F1 plants. Arrow with line indicates the interphase cell with no eccDNA hybridization signal. Arrows point to metaphase cells. (Scale bar, 10 µm.)

We found that the eccDNA in $F_1$ progeny displayed copy number variation ranging in number from 1 to 39 (FIG. 17 and FIG. 25). All progeny except one harbored eccDNAs but FISH signals on mitotic metaphase spreads prepared from a single root tip meristem were dramatically variable from cell to cell. We observed several FISH signal patterns in different cells (n=50) from a single root preparation of one plant (MHFS #1): i) eccDNAs were associated with most of chromosomes in 50% of the cells similar to the GR parent plant (FIGS. 15 & 16), ii) eccDNAs were associated with half of the chromosomes in 26% of the cells (FIG. 16b), iii) eccDNAs were associated with only a few of chromosomes in 16% of the cells (FIGS. 15 & 16c), and iv) all chromosomes were free of eccDNAs in 8% of the cells (FIG. 16d). Similar FISH patterns were detected on the metaphase cell spreads in all 20 $F_1$ plants (FIGS. 15 & 16). These results showed that eccDNAs varied in copy number due to missegregation during mitotic divisions and were not integrated into chromosomes.

EccDNAs Display Copy Number Variation in Different Tissues of a Plant.

Most surprisingly, qPCR analysis using genomic DNA prepared from leaf tissue showed that EPSPS copy number in five (MHFS #1, MHFS #2, MHFS #3, MHFS #6, MHFS #9) out of 10 $F_1$ plants was similar to the copy number found in GS plants (FIG. 17). However, FISH analysis from root tip meristems indicated that >90% of mitotic metaphase cells in these five plants had positive FISH signals (FIGS. 15 & 16).

Figure 18:
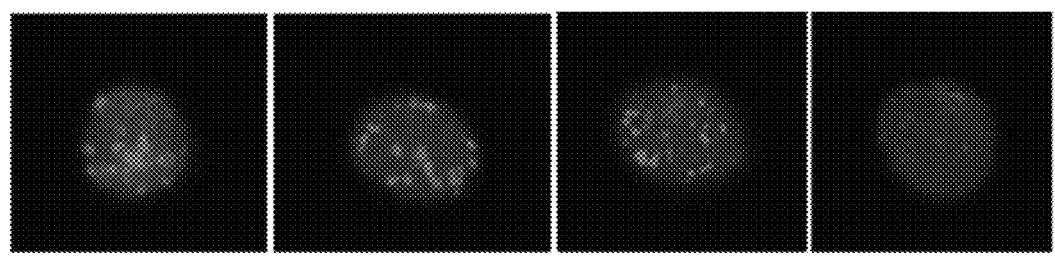
FIG. 18 shows images from FISH analysis on nuclei isolated from leaf tissue of plant MHFS #1 (top row), and FISH analysis on nuclei isolated from leaf tissue of plant MHFS #8 (bottom row) showing variable eccDNA signals. Note that 12% (n=100) and 71.4% (n=70) indicate the percentage of different cells having eccDNA associated with FISH positive nuclei in plants MHFS #1 and MHFS #8, respectively.
Figure 18:
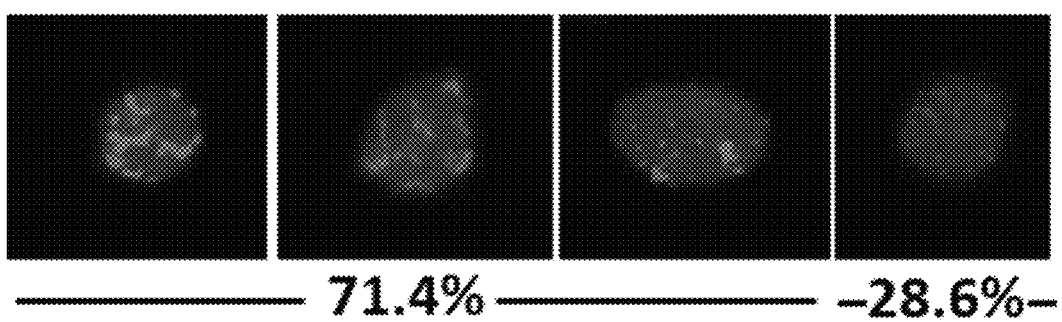

To resolve this apparent contradiction, we then performed FISH on nuclei isolated from leaf tissue of selected plants used in qPCR analysis (FIG. 18). The plant MHFS #1 with estimated one EPSPS copy showed positive FISH signals in 12% (n=100) of the nuclei isolated from the leaf tissue cells (FIG. 18, top row). The plant MHFS #8 with an estimated 31 EPSPS copies showed positive FISH signals in 71.4% (n=70) of the nuclei isolated from the leaf tissue cells (FIG. 18 bottom row).

Figure 19:
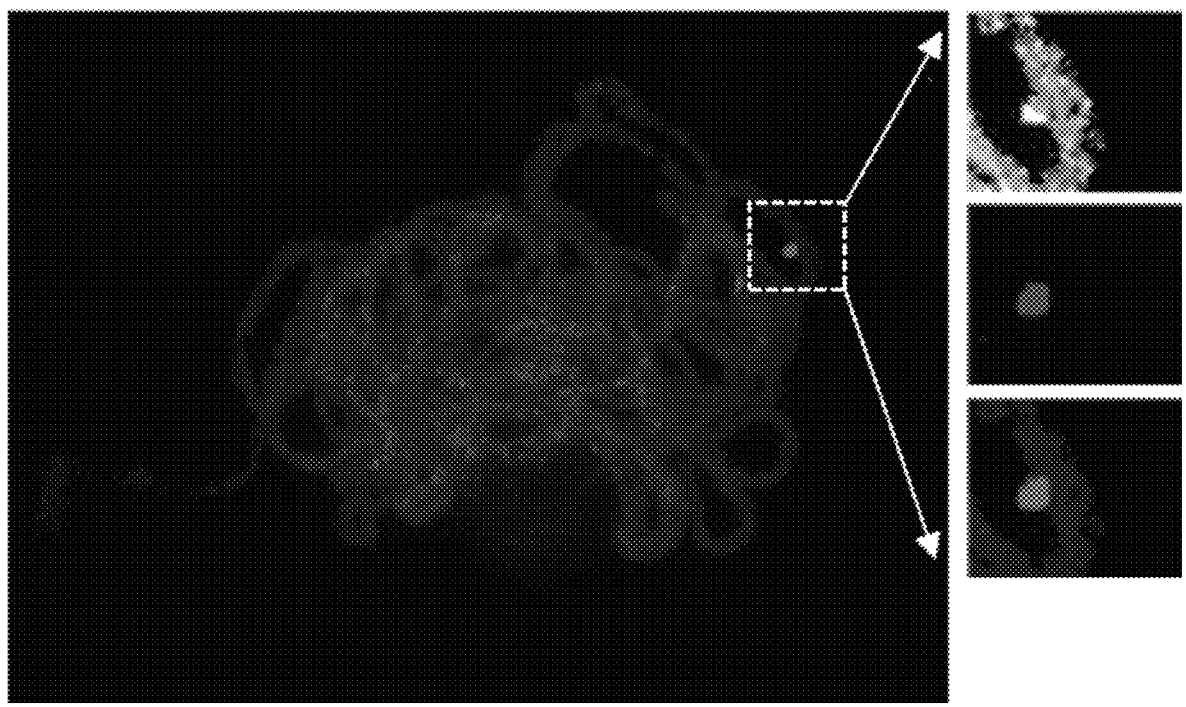
FIG. 19 is an image from FISH analysis showing anchoring of an eccDNA on pachytene chromosomes in plant MHFS #1.
Figure 27:
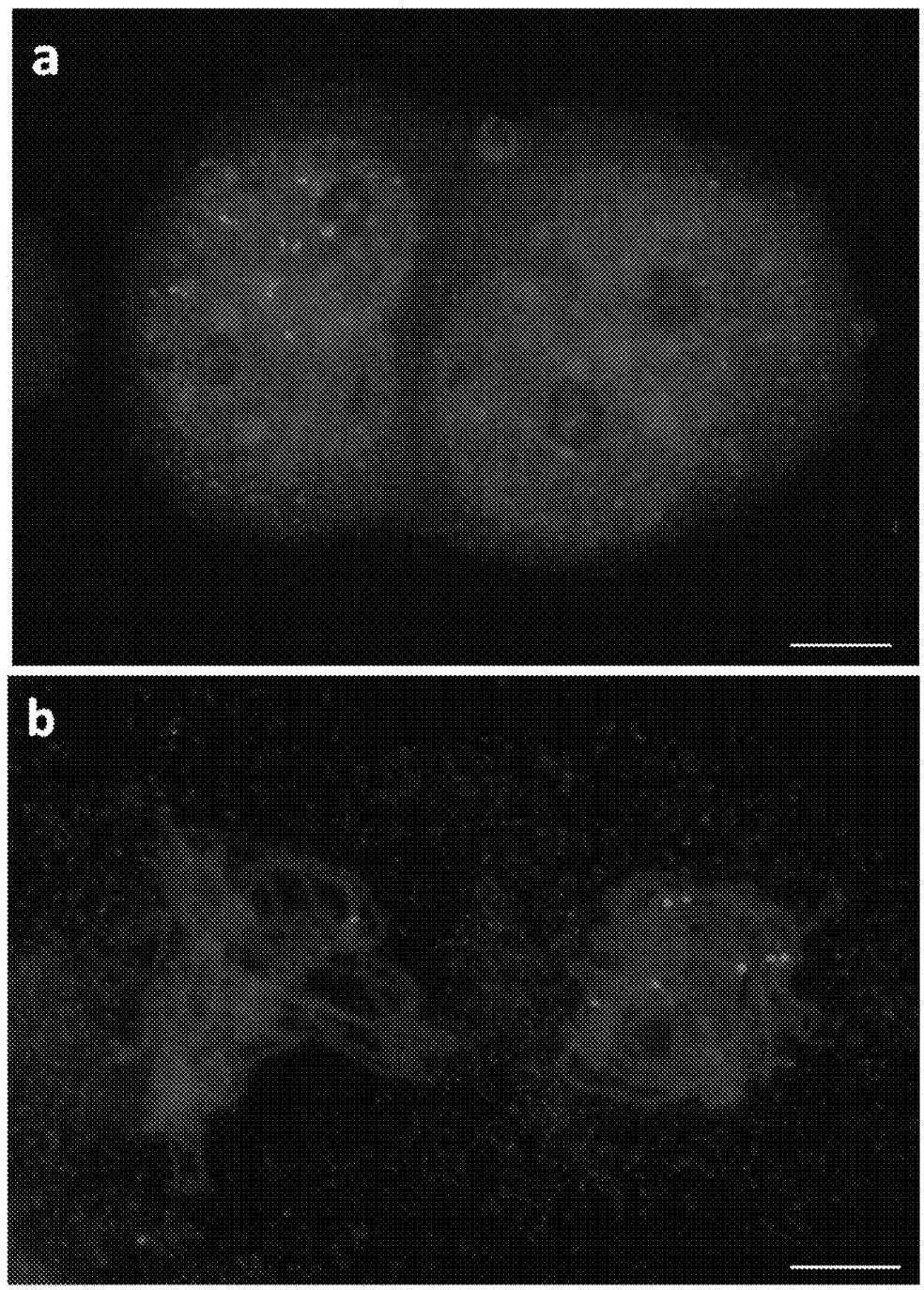
FIG. 27 shows images from FISH mapping of eccDNA (red signals) on tapetum (a) and pachytene (b) cells of plant MHFS 1. (Scale bars, 10 µm.)
Figure 28A:
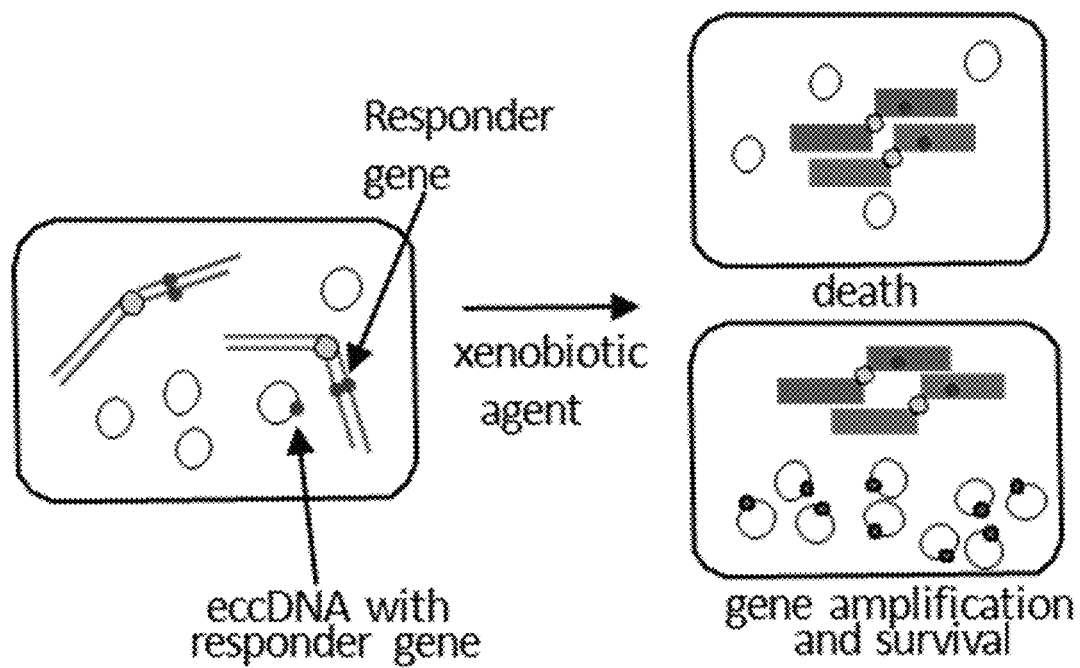
FIG. 28A is an illustration of eccDNA-mediated gene amplification.
Figure 28B:
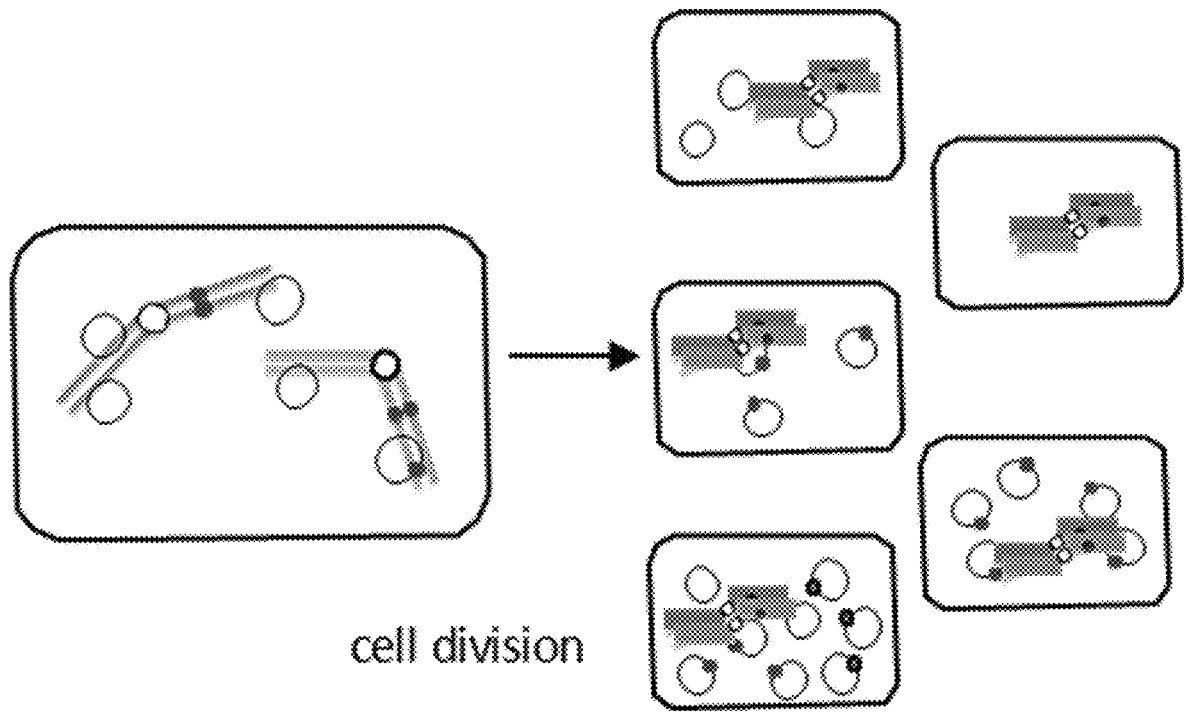
FIG. 28B is an illustration of anchoring of eccDNA on chromosomes and soma and germ cell variation.
Figure 28C:
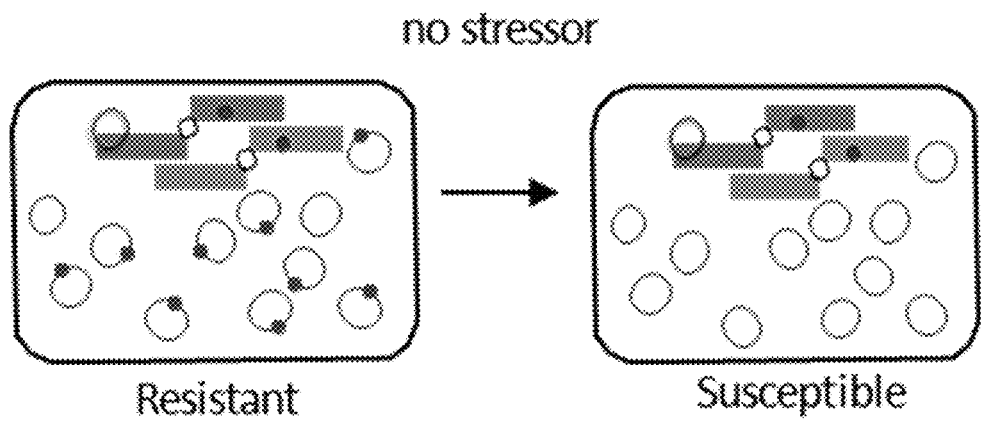
FIG. 28C is an illustration of using eccDNA knowledge for weed management for conversion of resistant to susceptible lines by withholding the stressor (e.g., glyphosate) and suppressing amplification of eccDNA.
Figure 28D:
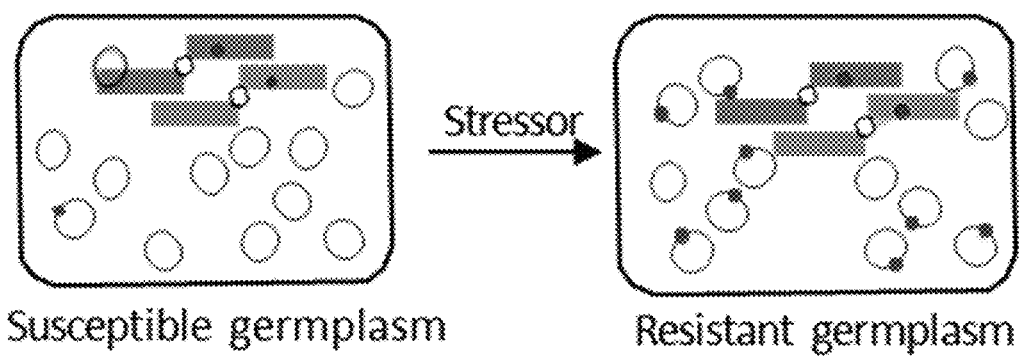
FIG. 28D is an illustration of using eccDNA for crop improvement by applying breeding techniques under stressors.
Figure 28E:
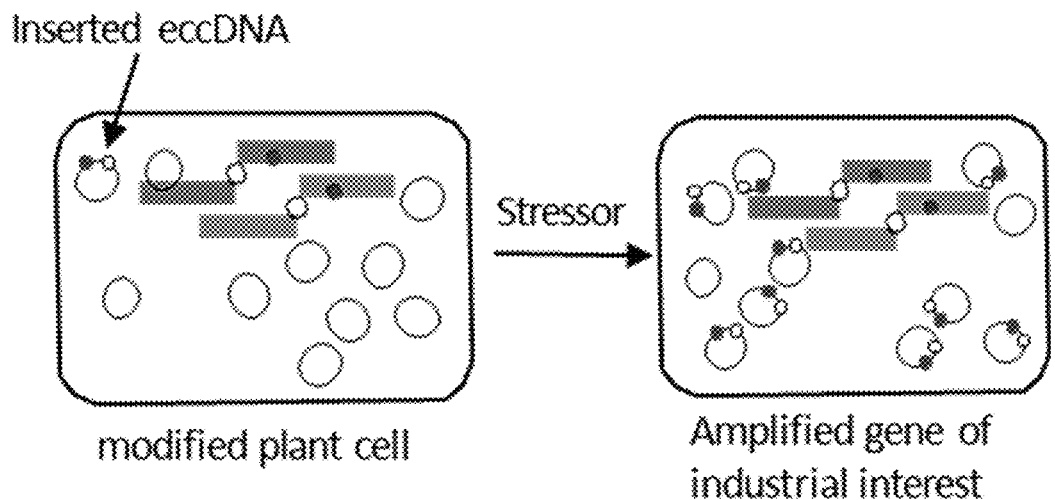
FIG. 28E is an illustration of using eccDNA for genetic engineering.

Next, we analyzed eccDNA variation in germ cells of plant MHFS #1 with estimated one copy of EPSPS gene. The results revealed that 12 out of 20 cells at pachytene stage of prophase I of meiosis showed eccDNAs ranging in number from 1 to 15, and 8 out of 20 of the cells were lacking eccDNAs (FIG. 19 & FIG. 27). In tapetum tissue, 7 out of 10 of the cells of this plant had eccDNAs. The frequency of eccDNAs in plant MHFS #1 was higher in mitotic root tip (92%) and meiotic cells (60-70%) than in cells from leaf tissue (12%), the reasons for this variation are not known except the former are actively dividing cells while the leaf is a non-dividing differentiated tissue.

DISCUSSION

This is the first report on the role of eccDNA driven gene amplification and rapid adaptive evolution in higher organisms. The lifestyle of higher organisms, including flowering plants and mammals, alternates between the dominant sporophytic phase and short lived gametophytic phase. The male and female gametophytes produce the gametes and transmit the genetic information and the zygotes develop into the sporophytes. The Darwinian evolution model acts on random, preexisting genetic variation in individuals and populations. In Darwinian evolutionary theory, there is no role of the life experience of the sporophyte or the inheritance of acquired characters as Lamarck had proposed. McClintock, based on her research on chromosome structure and behavior in soma and germ cells of maize, proposed that sporophytic genomes in fact can respond to challenges such as stress and this acquired genomic variation is transmitted to the germ cells. McClintock proposed " . . . presence of innate systems that are able to restructure a genome . . . to be triggered into action by form of stress . . . according to the nature of the challenge." We propose that eccDNA elements identified in this research are one component of McClintock's postulated innate system that rapidly produced soma variation, drove amplification of EPSPS genes in the sporophyte and were transmitted to germ cells and modulated rapid evolution of glyphosate resistance in *A. palmeri*.

Wahl proposed a general role of eccDNAs in gene amplification in mammalian and rodent cell lines for many different genes and selective drug agents. He proposed that eccDNAs may originate from chromosomes by deletions or circularization of blocked replicative forks, grow into double minutes (DMs) that are visible under the microscope, undergo unequal segregation during mitotic divisions in the presence of selective agents, and may integrate into the chromosomes to form homogenously staining regions (HSRs). Recent work on human cancer cell lines using combined whole genome sequencing and cytogenetic analysis has validated the essential role of eccDNA in oncogene amplification, heterogeneity and evolution of cancer. In yeast, 23% of the genome is represented in eccDNAs ranging in size from 1- to 38 kb and 80% of eccDNA contained autonomously replicating sequences. EccDNA have been documented in many plant species ranging in size from 2- to 20 kb containing tandem repeats suggesting their origin via intrachromosomal homologous recombination. Our results support widespread occurrence of eccDNA and its crucial role in gene amplification and plasticity of the sporophytic genome response to challenge.

Initial reports suggested that EPSPS amplicon was at least 30 kb in length, and contained MITEs, which were postulated to disperse the amplicon to each of the GR *A. palmeri* chromosomes at multiple sites. These authors interpreted EPSPS amplicon FISH signals as dispersed and integrated throughout the chromosome complement of *A. palmeri*. However, somatic metaphase chromosome-based analysis did not provide the resolution to detect the tethering of FISH signals to chromosomes. Using a marker chromosome tagged with 5S rDNA FISH signal, we observed random association of eccDNA signals to the marker chromosome. If the eccDNA was integrated into the chromosome, then they would display uniform signals in all cells, which was not the case (FIGS. 1-4). Moreover, during the pachytene stages of meiosis when chromosomes are highly elongated, the FISH signals were clearly observed as associated rather than part of the chromosome, and some were not associated with any chromosome at all (FIGS. 8-11). Finally, unequal mitotic segregation of eccDNAs produced variable FISH signals in different cells in the same preparation and some were lacking the signal (FIGS. 15-19 and FIG. 25-27). These data indicated that eccDNAs are not integrated into the chromosome and are autonomously replicating structures that display unequal mitotic segregation and thereby producing soma cell heterogeneity for resistance evolution.

Molin et al. prepared a BAC library from a GR *A. palmeri* biotype from Mississippi and sequencing of overlapping BACs revealed a 297 kb sequence unique to GR *A. palmeri* which they termed as "EPSPS cassette". The EPSPS cassette consisted of array of repetitive sequences, 72 putative genes and an autonomous replication sequences (ARS). EPSPS cassette-specific marker analysis revealed that glyphosate resistant biotypes across the USA had a single origin. Using overlapping BACs from the Mississippi biotype, our fiber-FISH analysis of a Kansas GR biotype clearly established that the EPSPS cassette is in fact an eccDNA (FIGS. 5-7 & 22-24). The shared common structure also supported a single origin of eccDNA of GR biotypes. The discovery of ARS sequences in eccDNA support our analysis of eccDNA behavior in dividing soma and germ cells leading to copy number variation. The EPSPS cassette also expressed HSC70 (heat shock protein) and NAC-containing protein genes which are heat, drought and salt stress-inducible. Thus, a single Georgia GR *A. palmeri* plant that acquired eccDNA 12 years ago, was indeed a supercharged weed biotype that could not only resist herbicide but also potentially withstand heat, drought and salt stress, and underwent a selection sweep and spread to many states in the USA in a short time frame.

Apart from copy number variation, eccDNAs displayed structural polymorphisms. The monomeric and dimeric circular forms were predominant (62%; 50% monomers and 12% dimers). The second largest population (30%) included linear forms (monomeric- and dimeric molecules) with a nearly intact structure as well as different sized linear molecules with different breakpoints in the eccDNA, or partial deletions. This number is likely overestimated because mechanical force during DNA fiber preparation can break circular molecules into linear forms. Nonetheless, it is possible that some linear molecules were generated from circular molecules associated with replication errors of the eccDNAs as was shown in the chloroplast genome. They could also represent rare chromosome integration events in evolutionary trajectory towards more stable acquired herbicide resistance. The remaining linear fibers (8%) were atypical eccDNAs with modified hybridization patterns. These may be the result of recombination events or random cleavage and fusion of replication intermediates, which has also been demonstrated in the chloroplast genome. These evolutionary dynamics of eccDNAs also suggest collection of smaller eccDNAs from different genomics regions can recombine and evolve into large eccDNA organelles under strong selection pressure.

The eccDNAs seem to have evolved the tethering mechanism for transmission to daughter cells during cell division. The eccDNAs were invariably associated with chromosomes and these associations were clearly observed in meiosis (FIGS. 12-13). The tethering is reminiscent of the behavior of autonomously replicating viruses, such as engineered plasmid vectors derived from Epstein-Barr virus (EBV) and bovine papillomavirus type1 (BPV1) in mammalian cell lines. Epstein-Barr nuclear antigen (EBNA1) and E2 proteins, that initiate replication from EBV- and BPV cis acting origin-of-replications (oriP), mediate anchoring to the host chromosomes. Mitotic chromosome tethering in mammalian cell lines transfected with engineered plasmid vector containing a mammalian scaffold/matrix-attached region (S/MAR) sequence and simian virus 40 (SV40) oriP have also been described. These observations raise the strong possibility that eccDNAs may also have cis acting sequences such as oriP that recruit cellular transacting factors to mediate chromosome association.

Hepadnaviruses, including human hepatitis B virus (HBV), possess a DNA genome and replicate through reverse transcription of an RNA intermediate, the pregenomic RNA (pgRNA). The pgRNA is transcribed from covalently closed circular DNA (cccDNA). The cccDNA exists as a stable episome which in turn is organized into minichromosomes by histone and non-histone proteins that are localized in the nuclei of infected hepatocytes. The cccDNAs are reverse transcribed into the relaxed-circle (RC) form of viral DNAs. The RC-DNAs can be reintegrated into the nuclei for amplification of their own cccDNAs. Similarly, the EPSPS cassette sequence harbors a reverse transcriptase gene long enough to encode a functional protein among other genes that may function in DNA replication. These products of transcription and reverse transcription may facilitate the RNA intermediates for amplification and assembly into DNA strands. These molecular mechanisms may facilitate the development of stable plant artificial chromosomes carrying agronomically useful traits. Furthermore, development of compounds that interfere with elements of tethering mechanism of eccDNAs to chromosomes may provide novel mechanisms of weed control.

Materials and Methods

Sampling of Glyphosate-Resistant *A. palmeri* and EPSPS Copy Determination.

*A. palmeri* plants used in this study were generated from seeds collected from a field near Manhattan, Kans., USA, where there was incident of lack of control of this population with glyphosate application in the previous season. This field was exposed to frequent applications of glyphosate in Roundup Ready soybean, grown in rotation. Seed of *A. palmeri* was randomly sampled from ten plants and pooled. Sixty seedlings from the above sample along with a known glyphosate-susceptible (GS) *A. palmeri* were germinated and seedlings were transplanted individually into Miracle-Gro potting mix (Marysville, Ohio) in 10 cm×10 cm×10 cm plastic pots and watered from top in a greenhouse (25/20° C. temperature; 15/9 h light day/night, supplemented with 120 mmol $m^{-2}s^{-1}$ illumination using sodium vapor lamps). At least 20 plants (10 to 12 cm tall) were treated separately with field use rate [868 g ae $ha^{-1}$ plus 2% (w/v) ammonium sulfate] or twice the field use rate of glyphosate. All treatments were applied with a moving single nozzle bench-type sprayer (Research Track Sprayer, De Vries Manufacturing, Hollandale, Minn.) equipped with a flat-fan nozzle tip (80015LP TeeJet tip, Spraying Systems Co., Wheaton, Ill.) delivering 168 L $ha^{-1}$ at 222 kPa in a single pass at 3.2 km h-1. Plant survival was assessed four weeks after treatment.

In response to glyphosate treatment [868 g ae ha' plus 2% (w/v) ammonium sulfate], plants showing injury levels of high (>80%) and low (<30%) in comparison to untreated check were grouped as GS and glyphosate-resistant (GR), respectively. To determine the number of EPSPS gene copies, at least four plants from each category along with known GS *A. palmeri* were selected and genomic DNA (gDNA) was isolated as follows. Fresh leaf tissue was collected from individual plants, flash frozen, and stored at −80° C. for genomic DNA (gDNA) isolation. gDNA was extracted from frozen leaf tissue (100 mg) using DNeasy Plant Mini Kit (Qiagen Inc., Valencia, Calif.) following the manufacturer's instructions. DNA was quantified on Nanodrop Spectrophotometer.

Quantitative PCR reaction was performed using a CFX96TM Real Time Detection System from BioRad to determine the EPSPS gene copy number in GR *A. palmeri* plants. qPCR reaction mix consisted of 8 µL of SYBR Green mastermix (Bio-Rad), 2 µL each of forward and reverse primers (5 and 2 µL of gDNA (15 ng $µL^{-1}$) to make the total reaction volume up to 14 µL. EPSPS gene copy number was measured relative to β tubulin gene (reference gene). PCR conditions were 95° C. for 15 min, and 40 cycles of 95° C. for 30 sec and 60° C. for 1 min. A meltcurve profile was included following the thermal cycling protocol to determine the specificity of the qPCR reaction. The following primer sequences were used:

| Primers | SEQ ID NO: |
|---|---|
| EPSPS 5' ATGTTGGACGCTCTCAGAACTCTTGGT 3' | 1 |
| EPSPS 5' TGAATTTCCTCCAGCAACGGCAA 3' | 2 |
| β tubulin 5' ATGTGGGATGCCAAGAACATGATGTG 3' | 3 |
| β tubulin 5' TCCACTCCACAAAGTAGGAAGAGTTCT 3' | 4 |

EPSPS gene copy number was measured with three technical replicates. Gene copy number was determined using the 2ΔCT method, where CT is the threshold cycle and ΔCT is CTTarget gene (EPSPS)−CTReference gene (β tubulin) (52). Several GR- and GS *A. palmeri* plants were selected for molecular cytogenetic mapping.

Reciprocal Hybridizations.

Male and female plants of GR- (carrying eccDNA) and GS *A. palmeri* (lacking eccDNA) were grown individually in Miracle-Gro potting mix (Marysville, Ohio) in 10 cm×10 cm×10 cm plastic pots and watered from the top in a greenhouse (25/20° C. temperature; 15/9 h light day/night, supplemented with 120 mmol $m^{-2}s^{-1}$ illumination using sodium vapor lamps). After flower initiation, the inflorescences of female GR and male GS plants and vice versa were covered together with plastic bread bags (33 cm×60 cm) containing micro-perforations. A total 10 $F_1$ plants for each reciprocal cross were randomly selected for FISH and qPCR analysis.

Bacterial Artificial Chromosome (BAC) Clones.

Clones of *A. palmeri* containing and flanking the EPSPS sequence were prepared. The clones were prepared from seedlings from a single plant from a Mississippi population demonstrating high glyphosate resistance. The BACs provided were 22F22 (contains EPSPS), 05K07, 01A02, 06D23, 13C09, 01G15, 08H14, and 23A10.

Slide Preparation.

Preparations of mitotic and meiotic chromosomes followed published protocols with minor modifications. Root tips were collected from plants and treated in a nitrous oxide gas chamber for 1.5 h. The root tips were fixed overnight in a 3:1 ethanol:glacial acetic acid and then squashed in a drop of 45% acetic acid. Young floral buds, about 1-2 mm long, were selected for meiotic chromosome preparations. Anthers from a single flower bud were squashed in 45% acetic acid on a slide and checked under a phase microscope. All preparations were stored at −70° C. until use.

Probe Labeling.

Sequences of *A. palmeri* EPSPS gene (GenBank accession no. JX564536) were used to develop the PCR primers for cloning of EPSPS gene. The PCR product was cloned in 2.1-TOPO TA vector (Invitrogen, Carlsbad, Calif.), and the clone was labeled with digoxigenin-11-deoxyuridine triphosphate (Roche Diagnostics, Indianapolis, Ind.) using a standard nick translation reaction. The clone, maize 5S rDNA was labeled with biotin-16-dUTP (Roche). The BAC clones were labeled with either biotin-16-dUTP or digoxigenin-11-dUTP using a nick translation reaction. Biotin- and digoxigenin-labeled probes were detected with Alexa Fluor 488 streptavidin antibody (Invitrogen) and rhodamine-conjugated anti-digoxigenin antibody (Roche), respectively.

Image Analysis.

Chromosomes were counterstained with 4',6-diamidino-2-phenylindole (DAPI) in Vectashield antifade solution (Vector Laboratories, Burlingame, Calif.). The images were captured with a Zeiss Axioplan 2 microscope (Carl Zeiss Microscopy LLC, Thornwood, N.Y.) using a cooled CCD camera Cool SNAP HQ2 (Photometrics, Tucson, Ariz.) and AxioVision 4.8 software. The final contrast of the images was processed using Adobe Photoshop CS5 software.

Fiber-FISH.

Young leaf tissues were collected from fast growing GR *A. palmeri* plants. Nuclei isolation, DNA fiber preparation, and fiber-FISH were performed following published protocols Fiber-FISH images were captured and processed as previously described in the FISH procedure.

Example 2

Extrachromosomal-Mediated Resistance to Herbicides and Novel Method for Weed Management As demonstrated in Example, 1 eccDNAs seem to be one of the components of McClintock's postulated innate systems that can rapidly produce soma variation, amplify EPSPS genes in the sporophyte that are transmitted to germ cells, and modulate rapid glyphosate resistance through genome plasticity and adaptive evolution.

In this Example, we have generated new data pertaining to the stability of eccDNAs carrying EPSPS in glyphosate-resistant (GR) *A. palmeri* plants in the absence of glyphosate selection. Such eccDNAs carrying EPSPS along with other stress response genes appears to be ubiquitous elements in *A. palmeri* as a source of copy number variation (CNV) and under intense selection drive rapid evolution of glyphosate resistance. This CNV in the absence of glyphosate selection, can lead to reversal of resistance to susceptibility because of reduction in EPSPS copies. We found glyphosate-susceptible (GS) (having 1 to 20 EPSPS copies) and glyphosate-resistant (GR) (>30 EPSPS copies) plants in progenies of hybrids derived from reciprocal crosses between GSxGR (with eccDNA) *A. palmeri*.

Approach:

To investigate the evolution of resistance to glyphosate in response to glyphosate selection pressure, we exposed GS plants (<20 EPSPS copies) to glyphosate for one generation to determine the EPSPS copy number and eccDNA variation in each generation and assess the possibility of evolution of resistance to continuous exposure to glyphosate via eccDNA containing EPSPS gene amplification. This process can be repeated for 6 to 8 generations. We also initiated experiments to examine the reversal of glyphosate resistance to susceptibility in the absence of glyphosate selection pressure by growing GR plants (>80-100 EPSPS copies) in the absence of glyphosate selection and generating progenies by random mating. This process can be repeated for 6 to 8 generations. A portion of progenies will be screened for susceptibility or resistance to glyphosate and determine the EPSPS gene copies and presence or absence of eccDNA in each generation.

Evolution of Resistance to Glyphosate in Response to Glyphosate Selection in GS Plants.

Approximately 1,009 seedlings were grown in greenhouse and treated with 0.25, 0.5 and 1× glyphosate (1×: 840 g ae/ha). The survivors have been selected for seed production of G-2 seed. Leaf tissue from 40 plants were collected for copy number analysis before the treatment with glyphosate. Additionally, the leaf samples were also collected from plants (at least 5) that survived glyphosate application.

Results:

| Glyphosate rate | Total treated plants | Dead | Alive | % survival |
| --- | --- | --- | --- | --- |
| 1X | 419 | 406 | 13 | 3 |
| 0.5X | 430 | 412 | 18 | 4 |
| 0.25X | 160 | 134 | 26 | 16 |

Reversal of Glyphosate Resistance to Susceptibility in the Absence of Glyphosate Selection in GR Plants.

The progeny generated from random mating of GR plants (>80-100 EPSPS copies) were used in this study. The seed collected from two GR plants (allowed to mate randomly) were planted and seedlings were generated. Approximately 100 plants from each GR plant were grown in the greenhouse without exposure to glyphosate for seed production. Additionally, approximately 127 seedlings from each of the above GR plant were also grown separately and treated with 1× dose of glyphosate to assess their response. Leaf tissue from 40 plants each was also collected for only EPSPS copy number analysis.

Results:

| | Total plants treated with 1x glyphosate | Dead | Alive | % survival |
| --- | --- | --- | --- | --- |
| GR1 | 127 | 41 | 86 | 68 |
| GR2 | 122 | 34 | 88 | 72 |

The invention claimed is:

1. A method of conferring glyphosate-resistance (GR) into plants, said method comprising transforming a plant cell with a stably incorporated artificial plant DNA construct by introducing into said plant cell an extrachromosomal circular plant DNA comprising a 5-enopyruvlyshikimate-3-phosphate synthase (EPSPS) gene, wherein said extrachromosomal circular plant DNA associates or tethers itself to an endogenous chromosome in said plant cell such that it is stably maintained and replicated extrachromosomally in said plant cell to yield a plurality of copies of said extrachromosomal circular plant DNA in said cell.

2. The method of claim 1, wherein said extrachromosomal circular plant DNA has a chromatin body that is tethered to a telomeric region of segregating chromosomes from anaphase to telophase during replication in said plant cell.

3. The method of claim 1, wherein said extrachromosomal circular plant DNA comprises cis acting sequences that recruit cellular transacting factors to mediate said chromosome association.

4. The method of claim 1, further comprising subjecting said plant cell to a stressor related to said glyphosate-resistance (GR), wherein exposure to said stressor promotes said association or tethering of said extrachromosomal circular plant DNA to a correct position on the endogenous chromosome in said plant cell for stable maintenance and replication extrachromosomally in said plant cell to confer said glyphosate-resistance (GR).

5. The method of claim 4, wherein said subjecting said plant cell to a stressor increases copy numbers of said extrachromosomal circular plant DNA in said plant.

6. The method of claim 5, further comprising isolating protein from said plant expressed from said extrachromosomal circular plant DNA.

7. The method of claim 1, further comprising regenerating modified plants from said modified cells.

8. The method of claim 7, further comprising subjecting said modified plants to a stressor related to said glyphosate-resistance (GR), wherein exposure to said stressor promotes selection of responder gene extrachromosomal circular plant DNA elements and/or association or tethering of said extrachromosomal circular plant DNA to a correct position on the endogenous chromosome in said modified plant for stable maintenance and replication extrachromosomally in said plant cells to confer said glyphosate-resistance (GR).

9. The method of claim 8, wherein said subjecting said modified plants to a stressor increases copy numbers of said extrachromosomal circular plant DNA in said plant.

10. The method of claim 1, wherein said transforming a plant cell comprises:
(a) culturing immature plant embryos to form callus tissue; and
(b) transforming said tissue with said artificial plant DNA construct to yield modified plant cells by introducing into said tissue said extrachromosomal circular plant DNA, wherein said extrachromosomal circular plant DNA associates or tethers itself to an endogenous chromosome in said plant cell such that it is stably maintained and replicated extrachromosomally in said plant cell; said method further comprising,
(c) regenerating modified plants from said modified plant cells, wherein said glyphosate-resistance (GR) is expressed in said modified plants.

11. A seed of a plant produced by the method of claim 10.

12. A modified plant cell produced by the method of claim 10.

13. A modified plant comprising an extrachromosomal circular plant DNA comprising a 5-enopyruvlyshikimate-3-phosphate synthase (EPSPS) gene conferring glyphosate-resistance (GR) when expressed in said plant, wherein said extrachromosomal circular plant DNA associates or tethers itself to an endogenous chromosome in said plant cell such that it is stably maintained and replicated extrachromosomally in said plant cell.

14. A vector comprising a nucleic acid construct comprising an extrachromosomal circular plant DNA comprising a 5-enopyruvlyshikimate-3-phosphate synthase (EPSPS) gene conferring glyphosate-resistance (GR) when expressed in a plant, wherein said extrachromosomal circular plant DNA is operably linked to an element that associates or tethers itself to an endogenous chromosome in a plant cell to drive extrachromosomal expression and replication in said plant cell.

15. A modified plant having stably incorporated the vector of claim 14 extrachromosomally associated or tethered to one or more endogenous chromosomes.

* * * * *